US012599700B2

(12) United States Patent　(10) Patent No.:　US 12,599,700 B2

Murray　(45) Date of Patent:　Apr. 14, 2026

(54) SYSTEM AND METHODS FOR CONNECTIVE TISSUE REPAIR USING SCAFFOLDS

(71) Applicant: The Children's Medical Center Corporation, Boston, MA (US)

(72) Inventor: Martha M. Murray, Sherborn, MA (US)

(73) Assignee: The Children's Medical Center Corporation, Boston, MA (US)

( * ) Notice: Subject to any disclaimer, the term of this patent is extended or adjusted under 35 U.S.C. 154(b) by 440 days.

(21) Appl. No.: 16/779,640

(22) Filed: Feb. 2, 2020

(65) Prior Publication Data

US 2020/0171203 A1　Jun. 4, 2020

Related U.S. Application Data

(63) Continuation-in-part of application No. 16/577,890, filed on Sep. 20, 2019, now Pat. No. 11,839,696, (Continued)

(51) Int. Cl.
*A61L 27/24*　(2006.01)
*A61B 17/16*　(2006.01)
(Continued)

(52) U.S. Cl.
CPC .......... *A61L 27/24* (2013.01); *A61B 17/1675* (2013.01); *A61F 2/08* (2013.01);
(Continued)

(58) Field of Classification Search
CPC .... A61F 2/08; A61F 2/0811; A61B 2017/564; A61L 27/24; A61L 27/3662; A61L 27/26; A61L 2430/10; A61K 35/14
See application file for complete search history.

(56) References Cited

U.S. PATENT DOCUMENTS 2,127,903 A　8/1938　Bowen
3,176,316 A　4/1965　Bodell
(Continued)

FOREIGN PATENT DOCUMENTS

CN　102488713 A　6/2012
EP　0295721 A2　12/1988
(Continued)

OTHER PUBLICATIONS

Fu et al.; Current Concepts for Rehabilitation following Anterior Cruciate Ligament Reconstruction; ACL Surgery & Rehabilitation; vol. 15, No. 6; Jun. 1992; pp. 270-278 (Year: 1992).*
(Continued)

*Primary Examiner* — Dinah Baria

(74) *Attorney, Agent, or Firm* — Offit Kurman; Mary K Nicholes

(57)　ABSTRACT

Methods and devices for repair of a torn or ruptured ligament using a scaffold device are provided. Aspects of the present disclosure include method of placement and fixation of sutures using a fixation device. In aspects of the present disclosure, the method includes notchplasty and delayed rehabilitation.

40 Claims, 9 Drawing Sheets

Related U.S. Application Data which is a continuation of application No. 15/679,
629, filed on Aug. 17, 2017, now Pat. No. 10,842,914,
which is a continuation of application No. 14/765,
064, filed as application No. PCT/US2014/014141 on
Jan. 31, 2014, now Pat. No. 9,757,495.

(60) Provisional application No. 61/759,868, filed on Feb.
1, 2013.

(51) Int. Cl.

| | |
|---|---|
| *A61F 2/08* | (2006.01) |
| *A61K 35/14* | (2015.01) |
| *A61L 27/26* | (2006.01) |
| *A61L 27/36* | (2006.01) |
| *A61L 27/56* | (2006.01) |
| A61B 17/56 | (2006.01) |
| A61F 2/28 | (2006.01) |
| A61K 38/00 | (2006.01) |

(52) U.S. Cl.
CPC .............. *A61K 35/14* (2013.01); *A61L 27/26*
(2013.01); *A61L 27/3633* (2013.01); *A61L
27/3662* (2013.01); *A61L 27/3691* (2013.01);
*A61L 27/56* (2013.01); *A61B 2017/564*
(2013.01); *A61F 2002/2835* (2013.01); *A61K
38/00* (2013.01); *A61L 2430/06* (2013.01);
*A61L 2430/10* (2013.01)

(56) References Cited

U.S. PATENT DOCUMENTS

| | | | |
|---|---|---|---|
| 3,195,778 | A | 7/1965 | Coates |
| 3,373,906 | A | 3/1968 | DeHart et al. |
| 3,545,008 | A | 12/1970 | Bader, Jr. |
| 3,587,982 | A | 6/1971 | Campbell |
| 3,738,535 | A | 6/1973 | Nicholls |
| 3,774,604 | A | 11/1973 | Danielsson |
| 3,797,499 | A | 3/1974 | Schneider |
| 3,805,300 | A | 4/1974 | Tascon-Alonso et al. |
| 3,893,834 | A | 7/1975 | Armstrong |
| 4,069,814 | A | 1/1978 | Clemens |
| 4,186,448 | A | 2/1980 | Brekke |
| 4,187,558 | A | 2/1980 | Dahlen et al. |
| 4,255,820 | A | 3/1981 | Rothermel et al. |
| 4,265,618 | A | 5/1981 | Herskovitz et al. |
| 4,326,540 | A | 4/1982 | Bailey et al. |
| 4,400,833 | A | 8/1983 | Kurland |
| 4,455,690 | A | 6/1984 | Homsy |
| 4,458,678 | A | 7/1984 | Yannas et al. |
| 4,467,806 | A | 8/1984 | Bhiwandiwala et al. |
| 4,469,101 | A | 9/1984 | Coleman et al. |
| 4,483,023 | A | 11/1984 | Hoffman, Jr. et al. |
| 4,578,067 | A | 3/1986 | Cruz, Jr. |
| 4,584,722 | A | 4/1986 | Levy et al. |
| 4,585,458 | A | 4/1986 | Kurland |
| 4,610,688 | A | 9/1986 | Silvestrini et al. |
| 4,642,119 | A | 2/1987 | Shah |
| 4,662,886 | A | 5/1987 | Moorse et al. |
| 4,713,075 | A | 12/1987 | Kurland |
| 4,731,084 | A | 3/1988 | Dunn et al. |
| 4,753,536 | A | 6/1988 | Spehar et al. |
| 4,775,380 | A | 10/1988 | Seedhom et al. |
| 4,808,184 | A | 2/1989 | Tepic |
| 4,808,570 | A | 2/1989 | Michaeli |
| 4,846,835 | A | 7/1989 | Grande |
| 4,851,513 | A | 7/1989 | Devore et al. |
| 4,883,486 | A | 11/1989 | Kapadia et al. |
| 4,894,063 | A | 1/1990 | Nashef |
| 4,917,699 | A | 4/1990 | Chervitz |
| 4,932,942 | A | 6/1990 | Maslanka |
| 4,944,755 | A | 7/1990 | Hennequin et al. |
| 4,946,377 | A | 8/1990 | Kovach |

| | | | | |
|---|---|---|---|---|
| 4,955,893 | A | | 9/1990 | Yannas et al. |
| 4,959,058 | A | | 9/1990 | Michelson |
| 4,973,321 | A | | 11/1990 | Michelson |
| 5,007,934 | A | | 4/1991 | Stone |
| 5,037,396 | A | | 8/1991 | Streeter |
| 5,078,744 | A | | 1/1992 | Chvpil |
| 5,078,745 | A | | 1/1992 | Rhenter et al. |
| 5,119,669 | A | | 6/1992 | Silvis et al. |
| 5,139,520 | A | * | 8/1992 | Rosenberg ......... A61B 17/1764 |
| | | | | 606/87 |
| 5,152,462 | A | | 10/1992 | Evans |
| 5,171,273 | A | | 12/1992 | Silver et al. |
| 5,171,274 | A | | 12/1992 | Fluckiger et al. |
| 5,176,708 | A | | 1/1993 | Frey et al. |
| 5,197,983 | A | | 3/1993 | Berman et al. |
| 5,206,023 | A | | 4/1993 | Hunziker |
| 5,206,028 | A | | 4/1993 | Li |
| 5,217,495 | A | | 6/1993 | Kaplan et al. |
| 5,275,826 | A | | 1/1994 | Badylak et al. |
| 5,281,422 | A | | 1/1994 | Badylak et al. |
| 5,306,301 | A | | 4/1994 | Graf et al. |
| 5,370,662 | A | | 12/1994 | Stone et al. |
| 5,376,118 | A | | 12/1994 | Kaplan et al. |
| 5,380,087 | A | | 1/1995 | Haber et al. |
| 5,436,135 | A | | 7/1995 | Tayot et al. |
| 5,445,833 | A | | 8/1995 | Badylak et al. |
| 5,455,833 | A | | 10/1995 | Herre et al. |
| 5,456,721 | A | | 10/1995 | Legrand |
| 5,458,636 | A | | 10/1995 | Brancato |
| 5,467,786 | A | | 11/1995 | Allen et al. |
| 5,474,450 | A | | 12/1995 | Chronister |
| 5,503,616 | A | | 4/1996 | Jones |
| 5,522,840 | A | | 6/1996 | Krajicek |
| 5,549,676 | A | | 8/1996 | Johnson |
| 5,556,429 | A | | 9/1996 | Felt |
| 5,595,621 | A | | 1/1997 | Light et al. |
| 5,652,077 | A | | 7/1997 | Obinata |
| 5,655,546 | A | | 8/1997 | Halpern |
| 5,681,353 | A | | 10/1997 | Li et al. |
| 5,688,276 | A | | 11/1997 | Shaffer |
| 5,713,374 | A | | 2/1998 | Pachence et al. |
| 5,749,895 | A | | 5/1998 | Sawyer et al. |
| 5,756,127 | A | | 5/1998 | Grisoni et al. |
| 5,800,543 | A | | 9/1998 | McLeod et al. |
| 5,810,884 | A | | 9/1998 | Kim |
| 5,855,619 | A | | 1/1999 | Caplan et al. |
| 5,897,591 | A | | 4/1999 | Kobayashi |
| 5,902,741 | A | | 5/1999 | Purchio et al. |
| 5,968,018 | A | | 10/1999 | Freeman et al. |
| RE36,370 | E | | 11/1999 | Li |
| 5,993,844 | A | | 11/1999 | Abraham et al. |
| 6,007,580 | A | | 12/1999 | Lehto et al. |
| 6,045,549 | A | | 4/2000 | Smethers et al. |
| 6,045,569 | A | | 4/2000 | Kensey et al. |
| 6,080,192 | A | | 6/2000 | Demopulos et al. |
| 6,087,113 | A | | 7/2000 | Caplan et al. |
| 6,096,309 | A | | 8/2000 | Prior et al. |
| 6,117,425 | A | | 9/2000 | MacPhee et al. |
| 6,129,757 | A | | 10/2000 | Weadock |
| 6,139,520 | A | | 10/2000 | McCrory et al. |
| 6,143,029 | A | | 11/2000 | Rippstein |
| 6,153,292 | A | | 11/2000 | Bell et al. |
| 6,171,610 | B1 | | 1/2001 | Vacanti et al. |
| 6,174,333 | B1 | | 1/2001 | Kadiyala et al. |
| 6,176,880 | B1 | | 1/2001 | Plouhar et al. |
| 6,203,572 | B1 | | 3/2001 | Johnson et al. |
| 6,214,047 | B1 | | 4/2001 | Melvin |
| 6,214,049 | B1 | | 4/2001 | Garyer et al. |
| 6,234,795 | B1 | | 5/2001 | Fischer |
| 6,280,474 | B1 | | 8/2001 | Cassidy et al. |
| 6,283,996 | B1 | | 9/2001 | Chervitz et al. |
| 6,309,372 | B1 | | 10/2001 | Fischer et al. |
| 6,365,149 | B2 | | 4/2002 | Vyakarnam et al. |
| 6,398,761 | B1 | | 6/2002 | Bills et al. |
| 6,454,129 | B1 | | 9/2002 | Green |
| 6,472,210 | B1 | | 10/2002 | Holy et al. |
| 6,517,578 | B2 | | 2/2003 | Hein |
| 6,592,623 | B1 | | 7/2003 | Bowlin et al. |
| 6,629,997 | B2 | | 10/2003 | Mansmann |

(56) References Cited

U.S. PATENT DOCUMENTS

| | | |
|---|---|---|
| 6,689,153 B1 | 2/2004 | Skiba |
| 6,699,214 B2 | 3/2004 | Gellman |
| 6,946,003 B1 | 9/2005 | Wolowacz et al. |
| 6,964,685 B2 | 11/2005 | Murray et al. |
| 6,971,787 B2 | 12/2005 | Botrie et al. |
| 6,989,034 B2 | 1/2006 | Hammer et al. |
| 7,119,062 B1 | 10/2006 | Alvis et al. |
| 7,148,209 B2 | 12/2006 | Hoemann et al. |
| 7,156,880 B2 | 1/2007 | Evans et al. |
| 7,250,057 B2 | 7/2007 | Forsberg |
| 7,335,220 B2 | 2/2008 | Khosravi et al. |
| 7,652,077 B2 | 1/2010 | Cook et al. |
| 7,838,630 B2 | 11/2010 | Murray et al. |
| 7,901,461 B2 | 3/2011 | Harmon et al. |
| 8,002,813 B2 | 8/2011 | Scarborough et al. |
| 8,070,827 B2 | 12/2011 | Shortkroff et al. |
| 8,137,686 B2 | 3/2012 | Kladakis et al. |
| 8,308,681 B2 | 11/2012 | Slocum et al. |
| 8,642,735 B2 | 2/2014 | Murray et al. |
| 8,652,171 B2 | 2/2014 | Stone et al. |
| 9,308,242 B2 | 4/2016 | Murray |
| 9,314,241 B2 | 4/2016 | Stone et al. |
| 9,414,833 B2 | 8/2016 | Stone et al. |
| 9,757,495 B2 | 9/2017 | Murray |
| 9,849,213 B2 | 12/2017 | Murray |
| 9,918,826 B2 | 3/2018 | Berelsman et al. |
| 9,918,827 B2 | 3/2018 | Berelsman et al. |
| 9,955,980 B2 | 5/2018 | Norton et al. |
| 10,092,288 B2 | 10/2018 | Denham et al. |
| 10,136,886 B2 | 11/2018 | Norton et al. |
| 10,675,016 B2 | 6/2020 | Coleman |
| 10,675,141 B2 | 6/2020 | Greenhalgh et al. |
| 10,702,260 B2 | 7/2020 | Sengun et al. |
| 10,729,430 B2 | 8/2020 | Denham et al. |
| 10,758,644 B2 | 9/2020 | Derwin et al. |
| 10,786,232 B2 | 9/2020 | Murray |
| 10,786,238 B2 | 9/2020 | Murray |
| 10,786,239 B2 | 9/2020 | Murray |
| 10,835,235 B2 | 11/2020 | Coleman |
| 10,842,914 B2 | 11/2020 | Murray |
| 11,076,845 B2 | 8/2021 | Murray |
| 11,076,846 B2 | 8/2021 | Murray |
| 11,484,578 B2 | 11/2022 | Murray et al. |
| 2001/0044659 A1 | 11/2001 | Laboureau et al. |
| 2002/0022884 A1 | 2/2002 | Mansmann |
| 2002/0038151 A1 | 3/2002 | Plouhar et al. |
| 2002/0055749 A1 | 5/2002 | Esnouf et al. |
| 2002/0123805 A1 | 9/2002 | Murray et al. |
| 2002/0161450 A1 | 10/2002 | Doi et al. |
| 2002/0183845 A1 | 12/2002 | Mansmann et al. |
| 2003/0012805 A1 | 1/2003 | Chen et al. |
| 2003/0023316 A1 | 1/2003 | Brown et al. |
| 2003/0033022 A1 | 2/2003 | Plouhar et al. |
| 2003/0078659 A1 | 4/2003 | Yang |
| 2003/0147935 A1 | 8/2003 | Binette et al. |
| 2003/0163144 A1 | 8/2003 | Weadock et al. |
| 2003/0167053 A1 | 9/2003 | Taufig |
| 2003/0212456 A1 | 11/2003 | Lipchitz et al. |
| 2003/0236573 A1 | 12/2003 | Evans et al. |
| 2004/0005297 A1 | 1/2004 | Connelly et al. |
| 2004/0024456 A1 | 2/2004 | Brown, Jr. et al. |
| 2004/0059416 A1 | 3/2004 | Murray et al. |
| 2004/0078077 A1 | 4/2004 | Binette et al. |
| 2004/0170664 A1 | 9/2004 | Spector et al. |
| 2004/0243235 A1 | 12/2004 | Goh et al. |
| 2004/0258729 A1 | 12/2004 | Czernuszka et al. |
| 2004/0262332 A1 | 12/2004 | Pauser et al. |
| 2004/0267362 A1 | 12/2004 | Hwang et al. |
| 2005/0025514 A1 | 2/2005 | Kitozaki |
| 2005/0027307 A1 | 2/2005 | Schwartz et al. |
| 2005/0100536 A1 | 5/2005 | Mishra |
| 2005/0129730 A1 | 6/2005 | Pang et al. |
| 2005/0183731 A1 | 8/2005 | Hunter et al. |
| 2005/0192581 A1 | 9/2005 | Molz et al. |
| 2005/0230422 A1 | 10/2005 | Muller et al. |
| 2005/0261736 A1 | 11/2005 | Murray et al. |
| 2005/0267521 A1 | 12/2005 | Forsberg |
| 2006/0190041 A1 | 8/2006 | Fallin et al. |
| 2007/0118217 A1 | 5/2007 | Brulez et al. |
| 2007/0150064 A1 | 6/2007 | Ruberte et al. |
| 2007/0269476 A1 | 11/2007 | Voytik-Harbin et al. |
| 2007/0288023 A1 | 12/2007 | Pelligrino et al. |
| 2008/0027542 A1 | 1/2008 | McQuillan et al. |
| 2008/0097430 A1 | 4/2008 | Bernstein et al. |
| 2008/0188936 A1 | 8/2008 | Ball et al. |
| 2008/0195205 A1 | 8/2008 | Schwartz |
| 2009/0143765 A1 | 6/2009 | Slocum et al. |
| 2009/0254104 A1 | 10/2009 | Murray |
| 2009/0306776 A1 | 12/2009 | Murray |
| 2010/0221835 A1 | 9/2010 | Tanaka et al. |
| 2011/0027338 A1 | 2/2011 | Murray et al. |
| 2011/0054524 A1 | 3/2011 | Beevers et al. |
| 2011/0184227 A1 | 7/2011 | Altman et al. |
| 2011/0295284 A1 | 12/2011 | Purdue et al. |
| 2011/0306555 A1 | 12/2011 | Murray et al. |
| 2012/0071975 A1 | 3/2012 | Gonzalez-Hernandez |
| 2012/0123474 A1 | 5/2012 | Zajac et al. |
| 2012/0201896 A1 | 8/2012 | Murray et al. |
| 2012/0283831 A1 | 11/2012 | Murray |
| 2013/0231609 A1 | 9/2013 | Slocum et al. |
| 2013/0273017 A1 | 10/2013 | Murray |
| 2014/0134249 A1 | 5/2014 | Murray et al. |
| 2014/0172096 A1 | 6/2014 | Koob et al. |
| 2014/0369984 A1 | 12/2014 | Murray et al. |
| 2015/0088198 A1 | 3/2015 | Spenciner et al. |
| 2015/0359530 A1 | 12/2015 | Moore |
| 2015/0367030 A1 | 12/2015 | Murray |
| 2016/0081790 A1 | 3/2016 | Cournoyer et al. |
| 2016/0206779 A1 | 7/2016 | Murray |
| 2016/0263279 A1 | 9/2016 | Murray et al. |
| 2016/0354195 A1 | 12/2016 | Spenciner |
| 2017/0143551 A1 | 5/2017 | Coleman |
| 2017/0156727 A1 | 6/2017 | Wilson-Wirth et al. |
| 2017/0281327 A1 | 10/2017 | Kaplan et al. |
| 2017/0340772 A1 | 11/2017 | Murray |
| 2017/0360437 A1 | 12/2017 | Ferguson et al. |
| 2018/0207316 A1 | 7/2018 | Murray |
| 2018/0228598 A1 | 8/2018 | Mathisen |
| 2019/0134269 A1 | 5/2019 | Murray et al. |
| 2019/0380693 A1 | 12/2019 | Burkhart |
| 2019/0388582 A1 | 12/2019 | Murray |
| 2020/0000573 A1 | 1/2020 | Whittaker et al. |
| 2020/0009292 A1 | 1/2020 | Murray |
| 2020/0196998 A1 | 6/2020 | Murray |
| 2020/0196999 A1 | 6/2020 | Murray |
| 2020/0214690 A1 | 7/2020 | Murray |
| 2020/0222586 A1 | 7/2020 | Murray |
| 2020/0253715 A1 | 8/2020 | Trenhaile |
| 2020/0345475 A1 | 11/2020 | Lima et al. |
| 2022/0096710 A1 | 3/2022 | Murray |

FOREIGN PATENT DOCUMENTS

| | | |
|---|---|---|
| EP | 0445951 A2 | 9/1991 |
| EP | 0645149 A1 | 3/1995 |
| EP | 1254671 A1 | 11/2002 |
| EP | 1273312 A1 | 1/2003 |
| EP | 3798226 A1 | 3/2021 |
| EP | 4162936 A1 | 4/2023 |
| GB | 2106794 A | 4/1983 |
| WO | 8500511 A1 | 2/1985 |
| WO | 9213565 A1 | 8/1992 |
| WO | 9311723 A1 | 6/1993 |
| WO | 9321857 A1 | 11/1993 |
| WO | 9525550 A1 | 9/1995 |
| WO | 9940771 A1 | 8/1999 |
| WO | 2000047130 A1 | 8/2000 |
| WO | 2000074760 A2 | 12/2000 |
| WO | 2001066130 A1 | 9/2001 |
| WO | 2002067812 A2 | 9/2002 |
| WO | 2003011107 A2 | 2/2003 |
| WO | 2003105737 A1 | 12/2003 |
| WO | 2004078134 A2 | 9/2004 |
| WO | 2006086479 A2 | 8/2006 |

(56)                References Cited

FOREIGN PATENT DOCUMENTS

| WO | 2007087353 A2 | 8/2007 | | |
| WO | 2008036393 A1 | 3/2008 | | |
| WO | 2008060361 A2 | 5/2008 | | |
| WO | 2008109407 A2 | 9/2008 | | |
| WO | 2008109807 A2 | 9/2008 | | |
| WO | 2010048418 A1 | 4/2010 | | |
| WO | 2010084481 A1 | 7/2010 | | |
| WO | 2010108237 A1 | 9/2010 | | |
| WO | 2013116744 A1 | 8/2013 | | |
| WO | 2014121067 A1 | 8/2014 | | |
| WO | 2018009634 A1 | 1/2018 | | |
| WO | WO-2018009637 A1 * | 1/2018 | ......... | A61B 17/0401 |

OTHER PUBLICATIONS

Al-Munajjed et al., Development of a collagen calcium-phosphate scaffold as a novel bone graft substitute, Royal College of Surgeons in Ireland, Jan. 1, 2008, 10 pp.

Anseth et al., Photopolymerizable degradable polyanhydrides with osteocompatibility, Nature Biotechnology, Feb. 1999, pp. 156-159, vol. 17.

Arendt et al., Knee Injury Patterns Among Men and Women in Collegiate Basketball and Soccer, The American Journal of Sports Medicine, American Orthopaedic Society for Sports Medicine, 1995, pp. 694-701, Vo. 23, No. 6.

Authorized Officer Athina Nickitas-Etienne, International Preliminary Report on Patentability, International Patent Application No. PCT/US2014/014141, May 13, 2014, 9 pp.

Authorized Officer Athina Nickitas-Etienne, International Preliminary Report on Patentability, International Patent Application No. PCT/US2006/004445, Feb. 17, 2009, 4 pp.

Authorized Officer Aurore Schneider, International Search Report and the Written Opinion, International Patent Application No. PCT/US2017/040865, Oct. 19, 2017, 8 pp.

Authorized Officer Brian Pellegrino, International Search Report, International Patent Application PCT/US2002/023885, Sep. 30, 2002, 3 pp.

Authorized Officer Brian Pellegrino, International Preliminary Examination Report, International Patent Application PCT/US2002/023885, Jan. 30, 2003, 3 pp.

Authorized Officer Ellen Moyse, International Preliminary Report on Patentability, International Patent Application No. PCT/US2007/001908, Jul. 29, 2008, 9 pp.

Authorized Officer Ellen Moyse, International Preliminary Report on Patentability, International Patent Application No. PCT/US2007/021009, Jan. 12, 2010, 13 pp.

Authorized Officer Lee W. Wong, International Search Report and the Written Opinion, International Patent Application No. PCT/US2007/001908, Sep. 5, 2007, 10 pp.

Authorized Officer Manuel A. Mendez, International Search Report and the Written Opinion, International Patent Application No. PCT/US2006/004445, Jun. 13, 2008, 5 pp.

Authorized Officer Monica Lopez Garcia, International Search Report and the Written Opinion, International Patent Application No. PCT/US2007/021009, Sep. 1, 2009, 18 pp.

Authorized Officer Ross Heosey, International Search Report and the Written Opinion, International Patent Application No. PCT/US2013/024467, Apr. 29, 2013, 12 pp.

Authorized Officer Shawn Lyons, International Search Report and the Written Opinion, International Patent Application No. PCT/US2014/014141, May 13, 2014, 14 pp.

Authorized Officer Simin Baharlou, International Preliminary Report on Patentability, International Patent Application No. PCT/US2017/040865, Jan. 8, 2019, 6 pp.

Buck, R.C., Regeneration of Tendon, The Journal of Pathology and Bacteriology, 1953, 22 pp., vol. LXVI, No. I.

Chamberlain et al., Early peripheral nerve healing in collagen and silicone tube implants: Myofibroblasts and the cellular response, Biomaterials 19, Elsevier, 1998, pp. 1393-1403.

Chamberlain et al., Collagen-GAG Substrate Enhances the Quality of Nerve Regeneration through Collagen Tubes up to Level of Autograft, Experimental Neurology 154, 1998, pp. 315-329, American Press.

Chamberlain, Lila Jo, Long Term Functional and Morphological Evaluation of Peripheral Nerves Regenerated Through Degradable Collagen Implants, MS Thesis, Massachusetts Institute of Technology, 1998, pp. 2.

Crapo et al., An overview of tissue and whole organ decellularization processes, NIH Public Access, Elsevier, Ltd., Biomaterials, Apr. 2011, pp. 3233-3243.

Cross et al., Dense type I collagen matrices that support cellular remodeling and microfabrication for studies of tumor angiogenesis and vasculogenesis in vitro, Biomaterials, 2010, pp. 8596-8507, Elsevier, Ltd.

Deie et al., High intrinsic healing potential of human anterior cruciate ligament, Acta Orthopaedica Scandinavica, 1995, pp. 28-32, vol. 66(1).

Desrosiers et al., Proliferative and Matrix Synthesis Response of Canine Anterior Cruciate Ligament Fibroblasts Submitted to Combined Growth Factors, Journal of Orthopaedic Research, The Journal of Bone and Joint Surgery, Inc., 1996, pp. 200-208, vol. 14, No. 2.

Dye, Scott F. MD, The Future of Anterior Cruciate Ligament Restoration, Clinical Orthopaedics and Related Research, Apr. 1996, pp. 130-139, vol. 325.

Extended European Search Report, European Patent Application No. 13743583.0, Sep. 17, 2015, 7 pp.

Extended European Search Report, European Patent Application No. 06720499.0, Completed Jul. 7, 2009, 7 pp.

Australian Examination Report, Australian Patent Application 2017254864, Aug. 31, 2018, 7 pp.

Partial European Search Report, European Patent Application 14745975.4, Aug. 26, 2016, 7 pp.

International Preliminary Report on Patentability, PCT/US2013/024467, Aug. 5, 2014, 7 pp.

Faryniarz et al., Myofibroblasts in the Healing Lapine Medical Collateral Ligament: Possible Mechanisms of Contraction, Journal of Orthopaedic Research, The Journal of Bone and Joint Surgery, Inc., 1996, pp. 228-238, vol. 14, No. 2.

Ferber, Dan, Lab-Grown Organs Begin to Take Shape, Science, Apr. 1999, 6 pp., The American Association for the Advancement of Science, vol. 284, No. 5413.

Ferber, Dan, Tissue Engineering: From the Lab to the Clinic, Science, Apr. 1999, 2 pp., The American Association for the Advancement of Science, vol. 284, No. 5413.

Ford et al., Autologous Collagen Vocal Fold Injection: A Preliminary Clinical Study, Sep. 1995, 944-948, Laryngoscope 105.

Frank et al., Natural History of Healing in the Repaired Medial Collateral Ligament, Journal of Orthopaedic Research, Orthopaedic Research Society, 1983, pp. 179-188, vol. 1, No. 2.

Geiger, et al., An In Vitro Assay of Anterior Cruciate Ligament (ACL) and Medial Collateral Ligament (MCL) Cell Migration, Connective Tissue Research, 1994, pp. 215-224, vol. 30. Gordon and Breach Science Publishers, S.A.

Gerich et al., Gene transfer to the patellar tendon, Knee Surg., Sports Traumatol, Arthroscopy, 1998, pp. 118-123, Springer-Verlag.

Gwinn et al., Relative Gender Incidence of Anterior Cruciate Ligament Injury at a Military Service Academy, 66th Annual Meeting of the American Academy of Orthopaedic Surgeons, Anaheim, CA, 1999, 1 pp., Paper No. 143.

Hefti et al., Healing of the Transected Anterior Cruciate Ligament in the Rabbit, The Journal of Bone and Joint Surgery, Mar. 1991, pp. 373-383, vol. 73-A, No. 3.

Itoh et al., Characterization of CO3AP-collagen sponges using X-ray high-resolution microtomography, Biomaterials, 2004, pp. 2577-2583, vol. 25.

Jackson et al., Biologic remodeling after anterior cruciate ligament reconstruction using a collagen matrix derived from demineralized bone: an experimental study in the goat model, The American Journal of Sports Medicine, Jul.-Aug. 1996, 15 pp., vol. 24, No. 4.

Juncosa-Melvin et al., The Effect of Autologous Mesenchymal Stem Cells on the Biomechanics an Histology of Gel-Collagen Sponge

(56) References Cited

OTHER PUBLICATIONS

Constructs Used for Rabbit Patellar Tendon Repair, Tissue Engineering, 2006, pp. 370-380, vol. 12.

Kanungo et al., Density-property relationships in mineralized collagen-glycosaminoglycan scaffolds, Aug. 26, 2008, pp. 1006-1018, Acta Biomaterials 5, Elsevier.

Kato et al., Formation of continuous collagen fibres: evaluation of biocompatibility ad mechanical properties, Biomaterials, Apr. 1990, pp. 169-175, vol. 11, Butterworth & Co., Ltd (Publishers).

Kawamoto et al., Selective migration of alpha-smooth muscle actin-positive myofibroblasts toward fibronectin in the Boyden's blindwell chamber, Clinical Science, 1997, pp. 355-362, vol. 93.

Kliment et al., A novel method for accurate collagen and biochemical assessment of pulmonary tissue utilizing one animal, Int. J. Clin. Exp. Pathol., 2011, pp. 349-355.

Louie, Libby K., Effect of a Porous Collagen-Glycosaminoglycan copolymer on Early Tendon Healing in a Novel Animal Model, Jan. 10, 1997, 1 pp., Ph.D. Thesis, Massachusetts Institute of Technology.

Louie et al., Development of a Collagen-GAG Copolymer Implant for the Study of Tendon Regeneration, Materials Research Society Symposium Proceedings, 1994, pp. 19-24, vol. 331.

Louie et al., Healing of Tendon Defects Implanted with a Porous Collagen=GAG Matrix: Histological Evaluation, Tissue Engineering, 1997, pp. 187-195, vol. 3, No. 2.

Marshall et al., The Anterior Ligament Cruciate Ligament: A Technique of Repair and Reconstruction, Clinical Orthopaedics and Related Research, Sep. 1979, pp. 97-106, No. 143.

Masur et al., Myofibroblasts differentiate from fibroblasts when plated at low density, Proc. Natl. Acad. Sci. USA, Apr. 1996, pp. 4219-4223, Cell Biology, vol. 93.

Murray et al., Migration Of Human Anterior Cruciate Ligament Fibrosis Into Porous Collagen-GAG Matrices In Vitro, 24th Annual Meeting of the Society for Biomaterials, San Diego, CA, Apr. 22-26, 1996, pp. 463.

Murray et al., The Migration of Human Anterior Cruciate Ligament Fibroblasts Into Porous Collagen-GAG Matrices In Vitro, 45th Annual Meeting, Orthopaedic Research Society, Anaheim, CA, Feb. 1-4, 1999, 1 pp.

Murray et al., Differences in the Outgrowth of Cells from Explants from the Proximal and Distal Human ACL and Responses to TGF-B1, 47th Annual Meeting, Orthopaedic Research Society, San Francisco, CA, Feb. 25-28, 2001, pp. 0788.

Murray et al., The Effects of Selected Growth Factors on Human ACL Cell Interactions with 3-D Collagen-GAG Scaffolds, 47th Annual Meeting, Orthodaedic Research Society, San Francisco, CA, Feb. 25-28, 2001, pp. 0790.

Murray et al., The migration of cells from the ruptured human anterior cruciate ligament into collagen-glycosaminoglycan regeneration templates in vitro, Biomaterials 22, 2001 Elsevier, pp. 2393-2402.

Murray et al., The Effect Ruptured Human Anterior Cruciate Ligament Histology on Cell Interactions with a Collagen-GAG Scaffold In Vitro, Davos Tissue Engineering Workshop, Davos Switzerland, 2000, I pp.

Murray et al., Histological Changes in the Human Anterior Cruciate Ligament After Rupture, The Journal of Bone and Joint Surgery Incorporated, Oct. 2000, pp. 1387-1397, vol. 82-A, No. 10.

Murray et al., Fibroblast Distribution in the Anteromedial Bundle of the Human Anterior Cruciate Ligament: The Presence of alpha smooth muscle actin-positive cells, J. Orthop. Res., 1999, pp. 18-27, vol. 17., No. 1.

Murray et al., Migration os Cells from Human Anterior Cruciate Ligament Explants into Collagen-Glycosaminoglycan Scaffolds, Journal of Orthopaedic Research, 2000., pp. 557-564, vol. 18, No. 4.

Murray et al., Migration of Cells fro mRuptured Human Anterior Curciate Ligament Explants Into Collagen-GAG Matrices, 6th World Biomatrials Conference, Kamuela, HI, 2000, 1 pp.

Murray et al., Use of a Collagen-Platelet Rich Plasma Scaffold to Stimulate Healing of a Central Defect in the Canine ACL, Journal of Orthopaedic Research, Apr. 2006, pp. 820-830, Wilet InterScience.

Nakamura et al., A Comparison of in vivo gene delivery methods for antisense therapy in ligament healing, Gene Therapy, 1998, pp. 1455-1461, vol. 5.

Nakamura et al., Early biological effect of in vivo gene transfer of platelet-derived growth factor (PDGF)-B into healing patellar ligament, Gene Therapy, 1998, pp. 1165-1170, vol. 5.

Neuman et al. The Determination of Hydroxyproline, J. Biol. Chem, 184, 1950, pp. 299-306.

Niklason et al., Functional arteries grown in vitro, Copyright American Association for the Advancement of Science, Washington, Apr. 16, 1999, 6 pp.

[No Author Listed], Guidance Document for Testing Biodegradable Polymer Implant Devices, ODE Guidance Documents, Apr. 20, 1996, 11 pp.

[No Author Listed], Meriam Webster Dictionary, Definition carbonate-apatite, 7 pp.

Noyes et al., Bone-Patellar Ligament-Bone and Fascia Lata Allografts for Reconstruction of the Anterior Cruciate Ligament, The Journal of Bone and Joint Surgery, 1990, pp. 1125-1136, vol. 72-A, No. 8.

Officer Anita Meacle, European Office Action, European Patent Application No. 07 867 174.0, Nov. 29, 2018, 5 pp.

Peter et al., Synthesis of poly (propylene fumarate) by acylation of propylebe glycol in the presence of a proton scavenger, Journal of Biomaterial Science, Polymer Edition, 1999, pp. 363-373, vol. 10, No. 3.

Qui et al. Outgrowth of chondrocytes from human articular cartilage explants and ecpression of alpha-smooth muscle actin, Wound Repair an d Regeneration, Sep.-Oct. 2000, pp. 383-391, vol. 8, No. 5.

Sadowska et al., Isolation of collagen from the skins of Baltic cod (*Gadus morhua*), Food Chemistry, 2003, pp. 257-262, Elsevier Science, Ltd.

Schmidt et al., Effect of Growth Factors on the Proliferation of Fibroblasts from the Medical Collateral and Anterior Cruciate Ligaments, Journal of Orthopaedic Research, The Journal of Bone and Joint Surgert, Inc., 1995, pp. 184-190, vol. 13, No. 2.

Schulz Torres et al., Effects of Modulus of Elasticity of Collagen Sponges on Their Cell-Mediated Contraction In Vitro, Massachusetts Institute of Technology, Jun. 1998, 96 pp.

Spindler et al., Comparison of Collagen Synthesis in the Peripheral and Central Region of the Canine Meniscus, Clinical Orthopaedics, Jun. 1994, pp. 256-263, vol. 303.

Spindler et al., Regional Mitogenic Response of the Meniscus to Platelet-Derived Growth Factor (PDGF-AB), Journal of Orthopaedic Research, The Journal od Bone and Joint Surgery, Inc., 1995, pp. 201-207, vol. 13, No. 2.

Spindler et al., Patellar Tendon and Anterior Cruciate Ligament Have Different Mitogenic Responses to Platelet-Derived Growth Factor and Transforming Growth Factor Beta, Journal of Orthpaedic Research, The Journal of Bone and Joint Surgery, Inc., 1996, pp. 542-546, vol. 14, No. 4.

Stensel et al., Collagen As A Biomaterial, Annual Review Biophysics Bioenginering, 1974, 24 pp.

Stevenson et al., Gender Differences in Knee Injury Epidemiology Among Competitive Alpine Ski Racers, The Iowa Orthopaedic Journal, 1998, pp. 64-66, vol. 18.

Stone et al., Future Directions Collagen-Based Prosteses for Meniscal Regeneration, Clinical Orthopaedics and Related Research, Mar. 1990, pp. 129-136, No. 252.

Stone et al., Regeneration of Meniscal Cartilage with Use of a Collagen Scaffold, The Journal of Bone and Joint Surgery, Incorporated, Dec. 1997, pp. 1770-1777, vol. 79-A, No. 12.

Suggs et al., Platelet adhesion on a bioresorbable poly (propylene fumarate-co-ethylene glycol) copolymer, Biomaterials 20, 1999, pp. 683-690, Elsevier Science Ltd.

Troxel, Karen S., Delay of Skin Would Contraction by Porous Collagen-GAG Matrices, (Ph.D. Thesis, Massachusetts Institute of Technology), 1994, 1 pp.

(56)         References Cited

OTHER PUBLICATIONS

Weadock et al., Physical crosslinking of collagen fibers: Comparison of ultraviolet irradiation and dehydrothermal treatment, Journal of Biomedical Materials Research, 1995, pp. 1373-1379, vol. 29.

Witkowski et al., Migration and Healing of Ligament Cells under Inflammatory Conditions, Journal of Orthopaedic Research, The Journal of Bone and Joint Surgery, Inc., 1997, pp. 269-277, vol. 15, No. 2.

Yannas, Ioannis V., Models of Organ Regeneration Processes Induced by Templates, Bioartificial Organs: Science, Medicine and Technology, 1997, pp. 280-293, The New York Academy of Sciences, New York, NY.

Yannas, Ioannis V., Regeneration of Skin and Nerve by Use of Collagen Templates, Collagen, Sep. 23, 2002, pp. 87-115, vol. III, No. 3345.

Yannas et al., Polymeric Template Facilitates Regeneration of Sciatic Nerve Across, The 11th Annual Meeting of the Society for Biomaterials, San Diego, CA, Apr. 25-28, 1985, pp. 146.

Yannas et al., Synthesis and characterization of a model extracellular matrix that induces partial regeneration of adult mammalian skin, Developmental Biology, Proc. Nat'l. Acad. Sci. USA, Feb. 1989. pp. 933-937, vol. 86, No. 3.

Extended European Search Report, European Patent Application No. EP 20195319, Report Completion Date Feb. 22, 2021, 11 pp.

Magarian et al., Delay of 2 or 6 Weeks Adversely Affects the Functional Outcome of Augmented Primary Repair of the Porcine Anterior Cruciate Ligament, The American Journal of Sports Medicine, 2010, pp. 2528-2534, vol. 38, No. 12.

Parkhurst et al., Quantification of human neutrophil motility int hree-dimensional collagen gels, Biophysical Journal, Feb. 1992, pp. 306-315, vol. 61.

Palmer et al. (Materials, 2011, 4, 1469-1482) (Year: 2011).

Vavken et al.(The Journal of Arthroscopic and Related Surgery, May 2012, vol. 28, No. 5, 672-680) (Year: 2012).

Website: https ://www.reprocell.com/product-catalog/koken-atelocollagen/atelocol lagen-bovi ne-dermis-acidic-solution, pp. 1-3, retrieved May 28, 2021 (Year: 2021).

Magarian E. M. et al., Am J Sports Med. 2010:38:2528-2534 (Year: 2010).

Sadowska, Food Chemistry 81 (2003) 257-262. (Year: 2003).

* cited by examiner

10

4

6

4

22

6

P

P

SYSTEM AND METHODS FOR CONNECTIVE TISSUE REPAIR USING SCAFFOLDS

CROSS-REFERENCE TO RELATED APPLICATIONS

The present application is a continuation-in-part of the U.S. application Ser. No. 16/577,890, filed on Sep. 20, 2019, which issued as U.S. Pat. No. 11,839,696, on Dec. 12, 2023, which is a continuation of U.S. application Ser. No. 15/679, 629, filed Aug. 17, 2017, which issued as U.S. Pat. No. 10,842,914, on Nov. 24, 2020, which is a continuation of U.S. application Ser. No. 14/765,064, filed Jul. 31, 2015, which issued as U.S. Pat. No. 9,757,495, on Sep. 12, 2017, which is a national stage entry under 35 U.S.C. § 371 of PCT Application No. PCT/US2014/014141, filed Jan. 31, 2014, which claims priority under 35 U.S.C. § 1.19(e) to and the benefit of U.S. Provisional Application Ser. No. 61/759,868, filed Feb. 1, 2013, and entitled Collagen Scaffolds. The entire contents of each application listed in this paragraph are incorporated herein by reference.

TECHNICAL FIELD

The present disclosure relates generally to systems and methods for connective tissue repair, and in particular to repair of a torn or ruptured connective tissue using a scaffold.

BACKGROUND

Intra-articular tissues, such as the anterior cruciate ligament (ACL), do not heal after rupture. In addition, the meniscus and the articular cartilage in human joints also often fail to heal after an injury. Tissues found outside of joints heal by forming a fibrin clot, which connects the ruptured tissue ends and is subsequently remodeled to form scar, which heals the tissue. Inside a synovial joint, a fibrin clot either fails to form or is quickly lysed after injury to the knee, thus preventing joint arthrosis and stiffness after minor injury. Joints contain synovial fluid which, as part of normal joint activity, naturally prevent clot formation in joints. This fibrinolytic process results in premature loss of the fibrin clot scaffold and disruption of the healing process for tissues within the joint or within intra-articular tissues.

The current treatment method for human anterior cruciate ligament repair after rupture involves removing the ruptured fan-shaped ligament and replacing it with a point-to-point tendon graft (ACL reconstruction). While this procedure can initially restore gross stability in most patients, longer follow-up demonstrates many post-operative patients have abnormal structural laxity, suggesting the reconstruction may not withstand the physiologic forces applied over time (Dye, 325 Clin. Orthop. 130-139 (1996)). The loss of anterior cruciate ligament function has been found to result in early and progressive radiographic changes consistent with joint deterioration (Hefti et al., 73A(3) J. Bone Joint Surg. 373-383 (1991)), and over 70% of patients undergoing ACL reconstruction develop osteoarthritis at only 14 years after injury (von Porat et al., Ann Rheum Dis. 63(3):269-73 (2004)). As anterior cruciate ligament rupture is most commonly an injury of a young athletes in their teens and twenties, early osteoarthritis in this group has difficult consequences.

In addition, anterior cruciate ligament reconstruction currently requires use of a tendon graft, harvested either from elsewhere in a patient's leg, or from a donor. Placement of this graft requires the removal of a large amount of the torn anterior cruciate ligament, thus removing the important proprioceptive nerve fibers which are important for ligament function, namely the dynamic stabilization of the knee. Placement of the graft is also recommended to be within the insertion site of the original anterior cruciate ligament, thus these zones of specialized tissue are also removed to create a tunnel for the graft.

As the tendon graft used in reconstruction surgery is often larger than the midsubstance width of the anterior cruciate ligament it is replacing, notchplasty is often performed as an ancillary surgical procedure to widen the intercondylar notch space to avoid graft impingement. The usefulness of notchplasty during anterior cruciate ligament reconstruction to fulfill the primary outcome of graft impingement, however, is still debated (Ranuccio et al., Joints 5(3):173-179 (2017)). Experienced ACL surgeons typically no longer perform notchplasty during ACL reconstruction (Scott, Insall & Scott Surgery of the Knee 48:637 (2017)), instead surgeons place the graft lower on the femur so that the larger graft does not impinge on the roof of the notch when the knee is extended (Tanksley et al., Orthop J Sports Med 5(5):2-8 (2017)).

Alternatively, for very proximal tears where the tibial stump of the anterior cruciate ligament can be compressed to the femoral insertion site (e.g. tibial stump length >90% of the ACL), it may be possible for the anterior cruciate ligament to heal with microfracture or sutures alone. However, the traditional suture repair of a torn anterior cruciate ligament promotes a high failure rate and increase knee laxity postoperatively (Gagliardi et al., Am J Sports Med. 47(3):560-566 (2019)).

Anterior cruciate ligament injuries may also be categorized as partial or complete tears. In partial tears of the anterior cruciate ligament, treatment is complicated by whether the surgical options discussed above for complete tears are warranted due to their associated risks and the risk of changing the partial tear to a complete tear during placement of the larger graft. An option in partial tears of the anterior cruciate ligament is to rest, protect the knee and let the ligament heal on its own.

In each case, ACL reconstruction, repair, or rest, the patient initiates physical therapy shortly after. Approximately 2 weeks after surgery, patients start physical therapy to recovery or maintain the strength of the surrounding muscles. Physical therapy aims to recover quadriceps strength and the most widely accepted PT protocol (the MOON ACL protocol) starts quadriceps strengthening with quadriceps sets and straight leg raises immediately after surgery. In addition, multiple researchers have recently reported the importance of complete recovery of quadriceps strength in the first few weeks after ACL surgery.

There is also growing interest in enhancing healing of ligaments using growth factors or to stimulate healing with the application of activated platelet-rich plasma (PRP). PRP is a combination of the extracellular matrix proteins normally found in plasma (including fibrinogen and fibronectin) and platelets. Prior studies evaluating the use of PRP typically have had a low red blood cell fraction (Dhurat et al., J Cutan Aesthet Surg, 7(4):189 (2014); Amable et al., Stem Cell Research & Therapy 4(3):67 (2013)). PRP has been shown to improve wound healing for other tissues. However, when evaluated for ACL repair or reconstruction, increasing the platelet count did not improve the strength of a repair ACL or improve the mechanical properties of an ACL graft (Fleming et al., Knee Surg Sports Traumatol Arthrosc. 23(4):1161-1170 (2015); Mastrangelo et al., J Orthop Res., 29(7):1002-1007 (2011)).

SUMMARY

Embodiments of the present disclosure include systems and methods that facilitate tissue regeneration and healing, and in particular, connective tissue regeneration or healing. It has been discovered that certain steps and procedures promote healing of an ACL ligament in where a biodegradable scaffold is placed in contact with a torn anterior cruciate ligament. In some embodiments, the method repairs an ACL wherein the tibial remnant has a tibial stump length of less than 75%, 50%, 25% or less than 10% of the total length of the ACL. In some embodiments, the method repairs an ACL with a tibial stump length that is greater than 5% of the total length of the ACL. In some embodiments of the present disclosure, the method repairs a partial tear of the ACL. In some other embodiments of the present disclosure, the method repairs a complete tear or rupture. In a complete tear or rupture, there are two ACL remnants, one on the tibia and the other on the femur. In other embodiments of the present disclosure, physical therapy is delayed post repair. Surprisingly, instead of initiating physical therapy 2 weeks after repair, a delay in physical therapy promoted healing of the ligament. This is especially seen in delay in quadriceps strength recovery. In some embodiments, physical therapy is not initiated until 3 to 12 weeks post repair.

In other embodiments of the present disclosure, notchplasty is performed during repair of the ACL. In some embodiments notchplasty is performed prior to contacting a scaffold to the torn portion of an ACL. In some embodiments, notchplasty is performed anteriorly, posteriorly and/or inferiorly on the intercondylar notch around the femoral insertion site of the ACL. In some embodiments, a kidney bean shape space is created on the intercondylar notch around the femoral insertion site of the ACL. In some embodiments, notchplasty is performed to remove 0.5 to 8 mm of bone from the intercondylar notch. In some embodiments, notchplasty removes as much bone material as would be performed for a 9 mm graft in ACL reconstruction. In some embodiments, notchplasty removes at least 3 mm anteriorly and as least 1 mm posteriorly and inferiorly from the intercondylar notch around the femoral insertion site of the ACL.

In other embodiments of the present disclosure a blood composition is introduced to a scaffold of the present disclosure. In some embodiments, the blood composition is autologous blood. In some embodiments, the blood composition comprises a modified blood composition, increasing or decreasing certain components of the blood. In some embodiments, the modified blood composition comprises increased monocytes, decrease eosinophils or a modification in the amount of other white blood cell types. In some embodiments, the modified blood composition introduced to a scaffold depends on a patient's sex.

Some embodiments of the method of the present disclosure comprises contacting a torn femoral stump and a torn tibial stump of the ACL with a scaffold by securing the torn tibial stump to a first end of a first suture, fixing a second end of the first suture and a first end of a second suture to a point on the femur near the femoral footprint, passing a second end of the second suture through the scaffold, fixing the second end of the second suture to a point on the tibia between the tibial spines and in the tibial ACL footprint, introducing a blood composition to the scaffold, sliding the scaffold along the second suture towards the back of the intercondylar notch to contact the torn femoral stump of the ACL, securing the second end of the second suture to the tibia to bring the tibia and femur into anatomic alignment, and pulling the torn tibial stump of the ACL to contact the scaffold.

Some embodiments of the method of the present disclosure comprises contacting a torn femoral stump and a torn tibial stump of the ACL with a compressible and biodegradable scaffold by forming a tibial tunnel from a point on the tibia between the tibial spines or in the tibial ACL footprint, forming a femoral tunnel from a point on the femur near or within the femoral ACL footprint, securing the torn tibial stump of the ACL to a first end of a first suture, passing a second end of the first suture and a first end of a first suture through the femoral tunnel, fixing the second end of the first suture and the first end of the second suture to the femur, passing a second end of the second suture through the scaffold and then through the tibial tunnel, fixing the second end of the second suture to the tibia, introducing a blood composition to the scaffold, sliding the scaffold along the second suture towards the back of the intercondylar notch to contact the torn femoral stump of the ACL, and pulling the torn tibial stump of the ACL to contact the scaffold In some embodiments, the point for suture fixation or for tunnel formation is near the anterior rim of the femoral ACL footprint. In some embodiments, the point for suture fixation or for tunnel formation is about halfway back or a third of the way back into the tibial ACL footprint.

BRIEF DESCRIPTION OF THE DRAWINGS

The foregoing summary, as well as the following detailed description, will be better understood when read in conjunction with the appended drawings. The drawings show illustrative embodiments of the disclosure. It should be understood, however, that the application is not limited to the precise arrangements and instrumentalities shown.

DETAILED DESCRIPTION OF ILLUSTRATIVE EMBODIMENTS

Embodiments of the present disclosure relate to systems, devices and methods for repairing a torn or ruptured connective tissue, such as a ligament. A system of the present disclosure may include a scaffold configured for the repair of a torn or ruptured tissue, one or more fixation devices, and one or more sutures. Systems and methods of the present disclosure may be used to treat either intra-articular or extra-articular injuries in a subject. Intra-articular injuries include, but are not limited to, meniscal tears, ligament tears and cartilage lesion. Extra-articular injuries include, but are not limited to, the ligament, tendon or muscle. Thus, the methods of the present disclosure may be used to treat injuries to the anterior cruciate ligament, the meniscus, labrum, for example glenoid labrum and acetabular labrum, cartilage, and other tissues exposed to synovial fluid after injury.

As used herein, an injury may be a torn ligament or a ruptured ligament. A torn ligament may be a partial tear. A torn ligament may also refer to a complete tear. A partial tear is one where a portion of the ligament is damaged, but the ligament remains connected. The tear may be of any length or shape. A ruptured ligament, also known as a complete tear, is one where the ligament has been completely severed providing two separate ends of the ligament. A ruptured ligament may provide two ligament ends of similar or different lengths. The rupture may be such that a ligament stump is formed at one end. For example, there may be a tibial stump connected to the tibia and a femoral stump connected to the femur.

Figure 1:
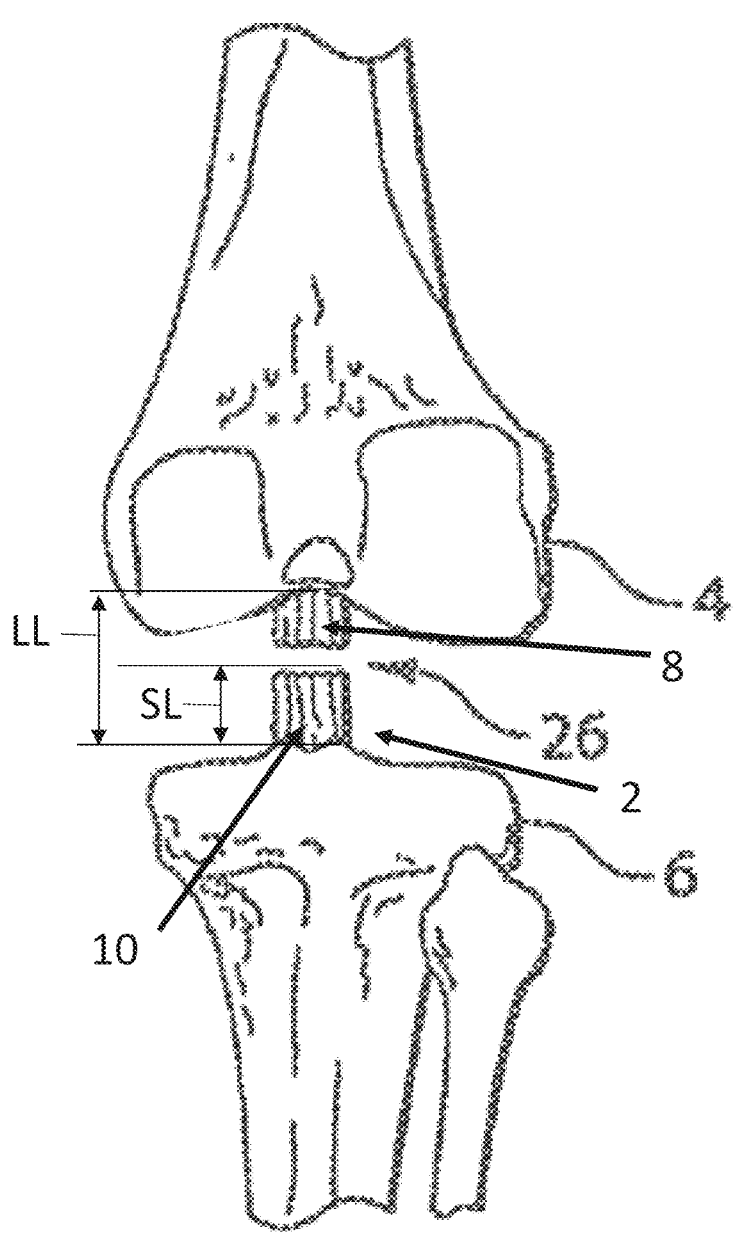
FIG. 1 is a schematic anterior view of a torn anterior cruciate ligament disposed between a femur and a tibia of a knee joint.

FIG. 1 illustrates an example of a ruptured anterior cruciate ligament in a knee joint according to an embodiment of the present disclosure. The knee joint as shown includes a femur 4 opposite a tibia 6 and an anterior cruciate ligament (ACL) 2. The ACL 2 is one of four strong ligaments that connects the bones of the knee joint. The function of the ACL is to provide stability to the knee and minimize stress across the knee joint. It restrains excessive forward movement of the lower leg bone, the tibia 6, in relation to the thigh bone, the femur 4, and limits the rotational movements of the knee.

The damaged or injured tissue may be treated with the collagen scaffolds described herein which are typically a sterile solution of solubilized collagen. Solubilized collagen, as used herein, is enzyme solubilized collagen including one or more of Type I, II, III, IV. V. X collagen. In various embodiments, the enzyme solubilized collagen is tropocollagen or atelocollagen rather than fibrillar collagen in order to reduce the antigenicity of the material. The collagen is isolated from a tissue source and mechanically minced and extracted as described above.

Figure 2:
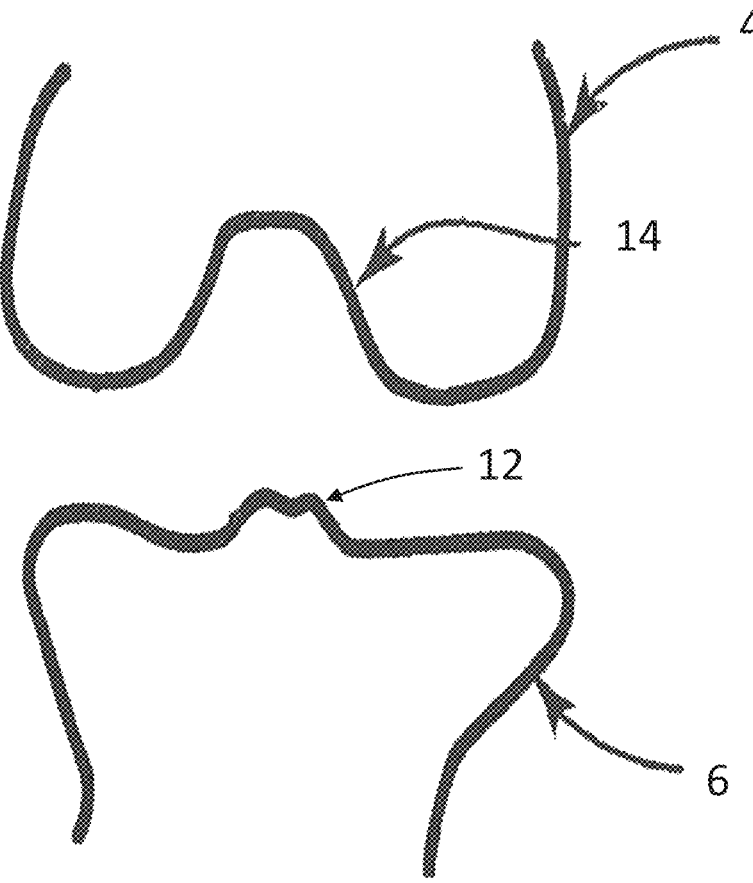
FIG. 2 is another schematic anterior view of the knee showing the distal femur, proximal tibia, intercondylar notch, and tibial spines.

As shown in FIG. 1, the anterior cruciate ligament 2 is ruptured such that it no longer forms a connection between the femur bone 4 and the tibia bone 6. The resulting ends of the ruptured ACL may be of any length. The ends may be of a similar length, or one end may be longer in length than the other. The end on the femur includes the femoral ACL stump 8. The end on the tibia includes a tibial stump 10. In some instances, it is believed that a repair is desirable when the tibial stump length SL is less than about 75% of the effective ligament length LL but greater than 5% of a total length LL of the ACL. The total length of the ACL is considered to be the length of ligament from femoral footprint to the tibial footprint along a linear axis. Turning to FIG. 2, the knee joint is shown with the ligament removed for illustrative purposes. As shown, the knee joint includes tibial spines 12 on the tibia 6 and the intercondylar notch 14 of the femur 4. In some instances, the methods as described herein may include performing a notchplasty of the intercondylar notch of the femur to provide space for larger ligament to form after surgical repair using a scaffold. It is a discovery of the inventors that such a notchplasty improves the size of the healing ligament, specifically resulting in a larger cross-sectional area of the ligament. As the mechanical strength of a ligament, and subsequently its ability to maintain the distance between the femur and tibia, is directly correlated with its cross sectional area, enlarging the notch with a notchplasty can help make a stronger repaired ACL and has been found by the inventors to be beneficial in ACL repair using a scaffold as described in the present disclosure.

Figure 3:
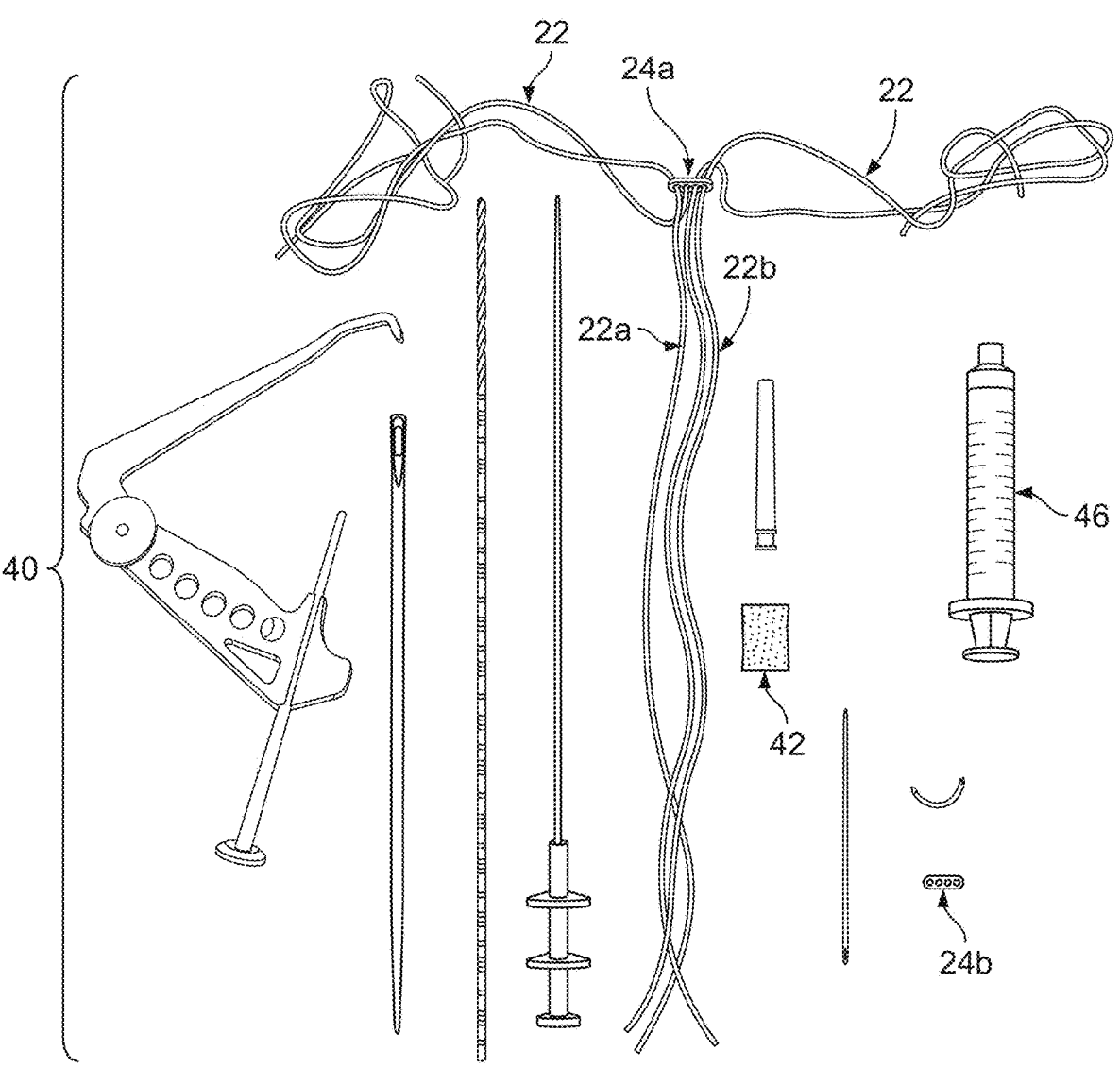
FIG. 3 illustrates an exemplary system used to repair tissue, according to an embodiment of the present disclosure.

Turning to FIGS. 1-3, a repair system 40 may be used to implant a scaffold 42 at a repair site 26 in the knee joint to facilitate repair of a ruptured connective tissue, such as, for example, a ruptured ACL. A repair site 26 is the area around a torn or ruptured ligament 2 into which a scaffold of the present disclosure may be inserted. A scaffold of the present disclosure can either fill the repair site 26 or partially fill the repair site 26. For example, a scaffold 42 can partially fill the repair site 26 when inserted and expand to fill the repair site 26 in the presence of a repair material. The repair material may be blood. In other examples, the repair material may be a blood composition, plasma or other fluids either present within the repair site 26, added to the scaffold, or added into the repair site 26.

As illustrated in FIG. 3, the repair system 40 may also include one or more sutures 22, such as a plurality of sutures 22a and 22b, to stabilize the tibial stump 10, femoral stump 8, and/or scaffold 42 in place, as further explained herein. In addition, one or more fixation devices 24a,24b may be use to secure the sutures 22 in place along the femur and tibia. The reference number 22 may be sometimes used interchangeably with reference number 22a and 22b. However, each suture may differ, for example, by color, absorption rate, etc. Referring to FIG. 3, various instruments may be used to facilitate repair. The system instruments may include various arthroscopic equipment. In one example, the system may include a syringe 46 for extracting blood from the patient and also for injecting blood into the scaffold. Other instruments may include a drill pin, a drill, a tibial aimer, a suture passer, one or more needles (e.g. a Keith Needle and Mayo Needle), and a foot kit.

A scaffold can be any shape that is useful for implantation into a subject. The scaffold, for instance, can be tubular, semi-tubular, cylindrical, including either a solid cylinder or a cylinder having hollow cavities, a tube, a flat sheet rolled into a tube so as to define a hollow cavity, liquid, an amorphous shape which conforms to that of the repair space, a "Chinese finger trap" design, a trough shape, or square. Other shapes suitable for the scaffold of the device as known to those of ordinary skill in the art are also contemplated in the present disclosure. In some examples, the scaffold 42 may form around a ruptured or torn ligament 2 at the repair site 26. For example, a scaffold 42 may be formed into a tube shape and wrapped around a ligament; a scaffold may be positioned behind the ligament such that the ligament is held within the scaffold; or a scaffold may be a "Chinese finger trap" design where one end is placed over a stump of a ruptured ligament and the second end placed over the other end of the ruptured ligament.

The scaffold, once implanted and combined with a repair material, allows the subject's body to develop a network of capillaries, arteries, and veins. Well-vascularized connective tissues heal with the migration of fibroblasts into the scaffold. The systems described herein provide a connection between a torn or ruptured ligament, which forms around a torn ligament, and promotes the repair of the ruptured or torn ligament which restores the integrity and structure of the ligament. The scaffold may be a three-dimensional (3-D) structure configured to repair torn or ruptured connective tissue. The scaffold provides a connection between the torn or ruptured portions of the tissue ligament and fibers, or forms around a torn ligament after injury, and encourages the migration of appropriate healing cells to form scar and new tissue in the scaffold. The scaffold may be a bioengineered substitute for a fibrin clot and is implanted, for example, between the ruptured ends of the ligament fascicles, or placed around a torn ligament. This substitute scaffold is designed to stimulate cell proliferation and extracellular matrix production in the gap between the ruptured ends of the ligament or the tear in the ligament, thus facilitating healing and regeneration of the injured ligament.

A scaffold that is configured for repair is one that is capable of being inserted into an area requiring repair and promotes regeneration of the ligament. A scaffold of the present disclosure is capable of insertion into a repair site and either forming a connection between the ends of a ruptured ligament, or forming around a torn ligament such that, in either case, the integrity and structure of the ligament is maintained. Regeneration offers several advantages over reconstruction, previously used to treat ligament injuries, including maintenance of the complex insertion sites and the unique fan-shape of the ligament, and preservation of remaining proprioceptive fibers within the ligament substance.

A scaffold may function either as an insoluble or biodegradable regulator of cell function or simply as a delivery vehicle of a supporting structure for cell migration or synthesis. The scaffold may be formed for a variety of matrices. Numerous matrices made of either natural or synthetic components have been investigated for use in ligament repair and reconstruction. Natural matrices are made from processed or reconstituted tissue components (such as collagens and GAGs). Because natural matrices mimic the structures ordinarily responsible for the reciprocal interaction between cells and their environment, they act as cell regulators with minimal modification, giving the cells the ability to remodel an implanted material, which is a prerequisite for regeneration.

Synthetic matrices are made predominantly of polymeric materials. Synthetic matrices offer the advantage of a range of carefully defined chemical compositions and structural arrangements. Some synthetic matrices are not degradable.

While the non-degradable matrices may aid in repair, non-degradable matrices are not replaced by remodeling and therefore cannot be used to fully regenerate ligament. It is also undesirable to leave foreign materials permanently in a joint due to the problems associated with the generation of wear particles, thus degradable materials are preferred for work in regeneration. Degradable synthetic scaffolds can be engineered to control the rate of degradation.

A scaffold is preferably made of a compressible, resilient material which has some resistance to degradation by synovial fluid. Synovial fluid as part of normal joint activity, naturally prevents clot formation. This fibrinolytic process would result in the premature degradation of the natural blood clot that stimulates healing of ligaments and other tissues outside of the synovial environment. This premature degradation of the provisional blood scaffold disrupts the healing process of the ligament. An implanted scaffold can either protect the blood from the synovial fluid environment and allow it to form a clot in the wound site to stimulate healing, or may contain other biologic stimuli to stimulate ligament healing. The scaffold material may be either permanent or biodegradable material, such as polymers and copolymers. The scaffold can be composed, for example, of collagen fibers, collagen gel, foamed rubber, natural material, synthetic materials such as rubber, silicone and plastic, ground and compacted material, perforated material, or a compressible solid material.

A scaffold may be a solid material such that its shape is maintained, or a semi-solid material capable of altering its shape and or size. A scaffold may be made of expandable material allowing it to contract or expand as required. The material can be capable of absorbing plasma, blood, other body fluids, liquid, hydrogel, or other material the scaffold is contacted with or is added to the scaffold.

A scaffold material can be protein, lyophilized material, or any other suitable material. A protein can be synthetic, bioabsorbable or a naturally occurring protein. A protein includes, but is not limited to, fibrin, hyaluronic acid, elastin, extracellular matrix proteins, or collagen. A scaffold material may be plastic or self-assembling peptides. A scaffold material may incorporate therapeutic proteins including, but not limited to, hormones, cytokines, growth factors, clotting factors, anti-protease proteins (e.g., alpha1-antitrypsin), angiogenic proteins (e.g., vascular endothelial growth factor, fibroblast growth factors), antiangiogenic proteins (e.g., endostatin, angiostatin), and other proteins that are present in the blood, bone morphogenic proteins (BMPs), osteoinductive factor (IFO), fibronectin (FN), endothelial cell growth factor (ECGF), cementum attachment extracts (CAE), ketanserin, human growth hormone (HGH), animal growth hormones, epidermal growth factor (EGF), interleukin-1 (IL-1), human alpha thrombin, transforming growth factor (TGF-beta), insulin-like growth factor (IGF-1), platelet derived growth factors (PDGF), fibroblast growth factors (FGF, bFGF, etc.), and periodontal ligament chemotactic factor (PDLGF), for therapeutic purposes. A lyophilized material is one that is capable of swelling when liquid, gel or other fluid is added or comes into contact with it.

Many biological materials are available for making the scaffold, including collagen compositions (either collagen fiber or collagen gel), compositions containing glycosaminoglycan (GAG), hyaluran compositions, and various synthetic compositions. Collagen-glycosaminoglycan (CG) copolymers have been used successfully in the regeneration of dermis and peripheral nerve. Porous natural polymers, fabricated as sponge-like and fibrous scaffolds, have been investigated as implants to facilitate regeneration of selected musculoskeletal tissues including ligaments. A scaffold, such as a sponge scaffold, may also be made from tendon (xenograft, allograft, autograft) or ligament or skin or other connective tissue which could be in the native state or processed to facilitate cell ingrowth or other biologic features. In one example, the scaffold is a collagen scaffold that is free of cross-links.

Any of the collagen materials described herein can be substantially free of one or more of the following: nucleic acid (DNA and/or RNA), glycosaminoglycan (GAG), phospholipid, active pepsin, and active virus. In other embodiments, the collagen material can have a substantially reduced level of one or more of the following: nucleic acid (DNA and/or RNA), glycosaminoglycan (GAG), phospholipid, active pepsin, and active virus. In one example, the content of phospholipid in the collagen material is less than 20% (e.g., less than 15%, 10%, 5%, or 1%) of that found in a native tissue. The content of phospholipid in the collagen material can be less than 10,000 $\mu$M/mg, 5,000 $\mu$M/mg, 2,500 $\mu$M/mg, 1,250 $\mu$M/mg, 1,000 $\mu$M/mg, 500 $\mu$M/mg, 125 $\mu$M/mg, or 50 $\mu$M/mg. In another example, the content of nucleic acids (e.g., DNA or RNA) in the collagen material is less than 20% (e.g., less than 15%, 10%, 5%, or 1%) of that found in a native tissue. The content of nucleic acids in the collagen material can be less than 700 $\mu$g/g, 350 $\mu$g/g, 200 $\mu$g/g, 100 $\mu$g/g, 35 $\mu$g/g, 10 $\mu$g/g, 5 $\mu$g/g, 1 $\mu$g/g, 0.5 $\mu$g/g, or 0.25 $\mu$g/g. In yet another example, the level of active pepsin in the material is less than 10,000 $\mu$g/ml (e.g., 1,000 $\mu$g/ml or 200 $\mu$g/ml). In still another example, the content of GAG in the collagen material is less than 50% of the total material (e.g., less than 40%, 30%, 20%, 10%, or 5%).

In aspects of the present disclosure, a scaffold is composed of a sponge or sponge-like material. A sponge scaffold may be absorbable or nonabsorbable. A sponge scaffold may be collagen, elastin, extracellular matrix protein, plastic, or self-assembling peptides. A sponge scaffold may be hydrophilic. A sponge scaffold is capable of compression and expansion as desired. For example, a sponge scaffold may be compressed prior to or during implantation into a repair site. A compressed sponge scaffold allows for the sponge scaffold to expand within the repair site. A sponge may be lyophilized and/or compressed when placed in the repair site and expanded once in place. The expansion of a sponge scaffold may occur after contact with blood or other fluid in the repair site or added to the repair site. A sponge scaffold may be porous. A sponge scaffold may be saturated or coated with a liquid, gel, or hydrogel repair material prior to implantation into a repair site. Coating or saturation of a sponge scaffold may ease implantation into a relatively undefined defect area as well as help to fill a particularly large defect area. A sponge scaffold may be composed of collagen. In a preferred embodiment, a sponge scaffold is treated with hydrogel. Examples of scaffolds and repair materials useful according to the present disclosure are found in U.S. Pat. No. 6,964,685 and US Patent Application Nos. 2004/0059416 and 2005/0261736, the entire contents of each are herein incorporated by reference.

Natural matrices may be matrices made predominantly from collagen, the main structural component in ligament. Collagen can be of the soluble or the insoluble type. Preferably, the collagen is soluble, e.g., acidic or basic. For example, the collagen can be type I, II, III, IV, V, IX or X. Preferably the collagen is type I. Type I collagen is the predominant component of the extracellular matrix for the human anterior cruciate ligament and provides an example of a choice for the basis of a bioengineered scaffold.

Collagen occurs predominantly in a fibrous form, allowing design of materials with very different mechanical properties by altering the volume fraction, fiber orientation, and degree of cross-linking of the collagen. The biologic properties of cell infiltration rate and scaffold degradation may also be altered by varying the pore size, degree of cross-linking, and the use of additional proteins, such as glycosaminoglycans, growth factors, and cytokines. In addition, collagen-based biomaterials can be manufactured from a patient's own skin, thus minimizing the antigenicity of the implant (Ford et al., 105 Laryngoscope 944-948 (1995)).

Figure 5:
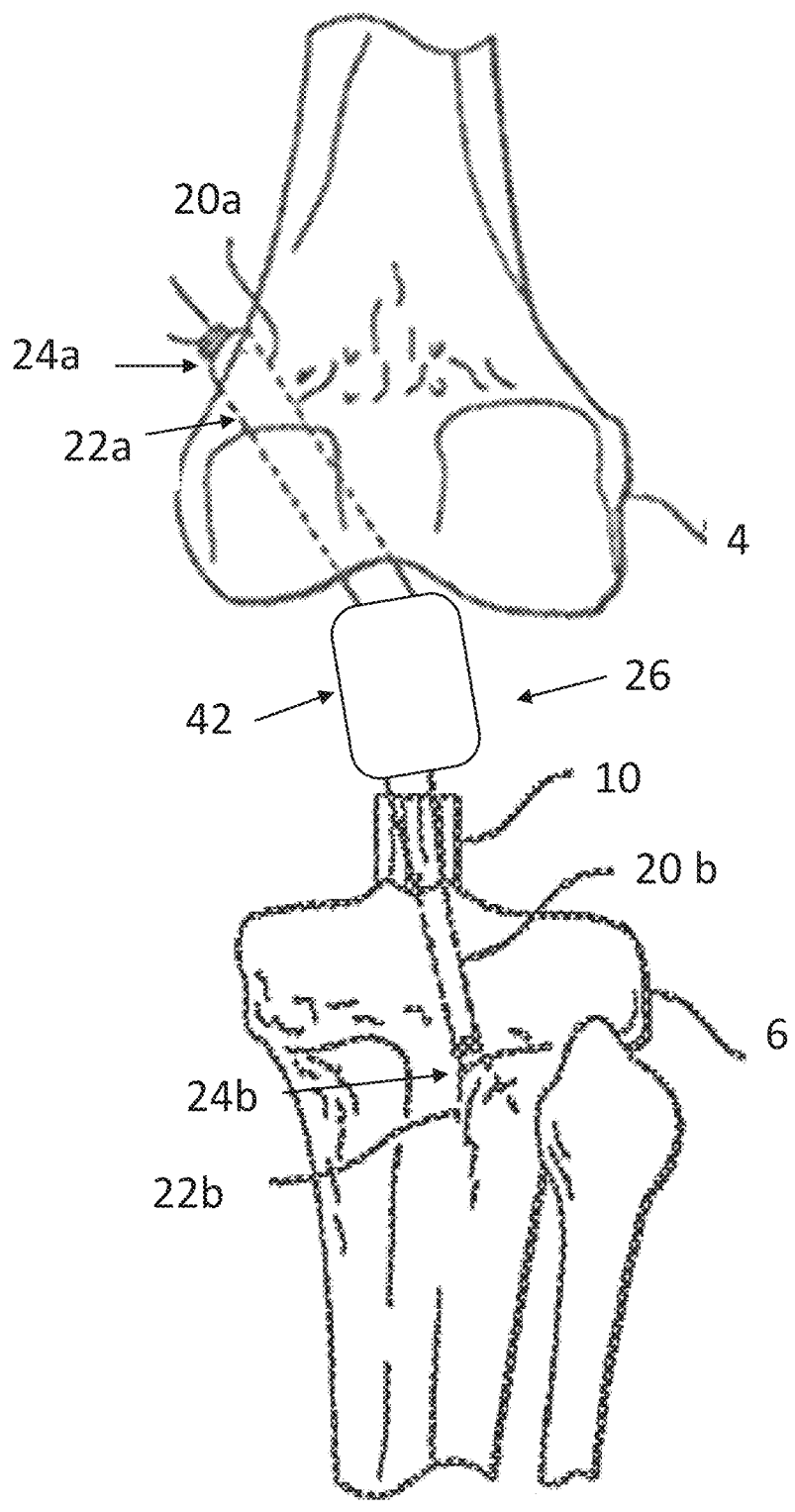
FIG. 5 is a schematic view of sutures and a fixation device attached to the surface of the femur with sutures extending through a drill hole in the femur, a fixation device attached to the tibia with the sutures extending through a drill hole in the tibia, and a scaffold in the repair site.
Figures 6A, 6B:
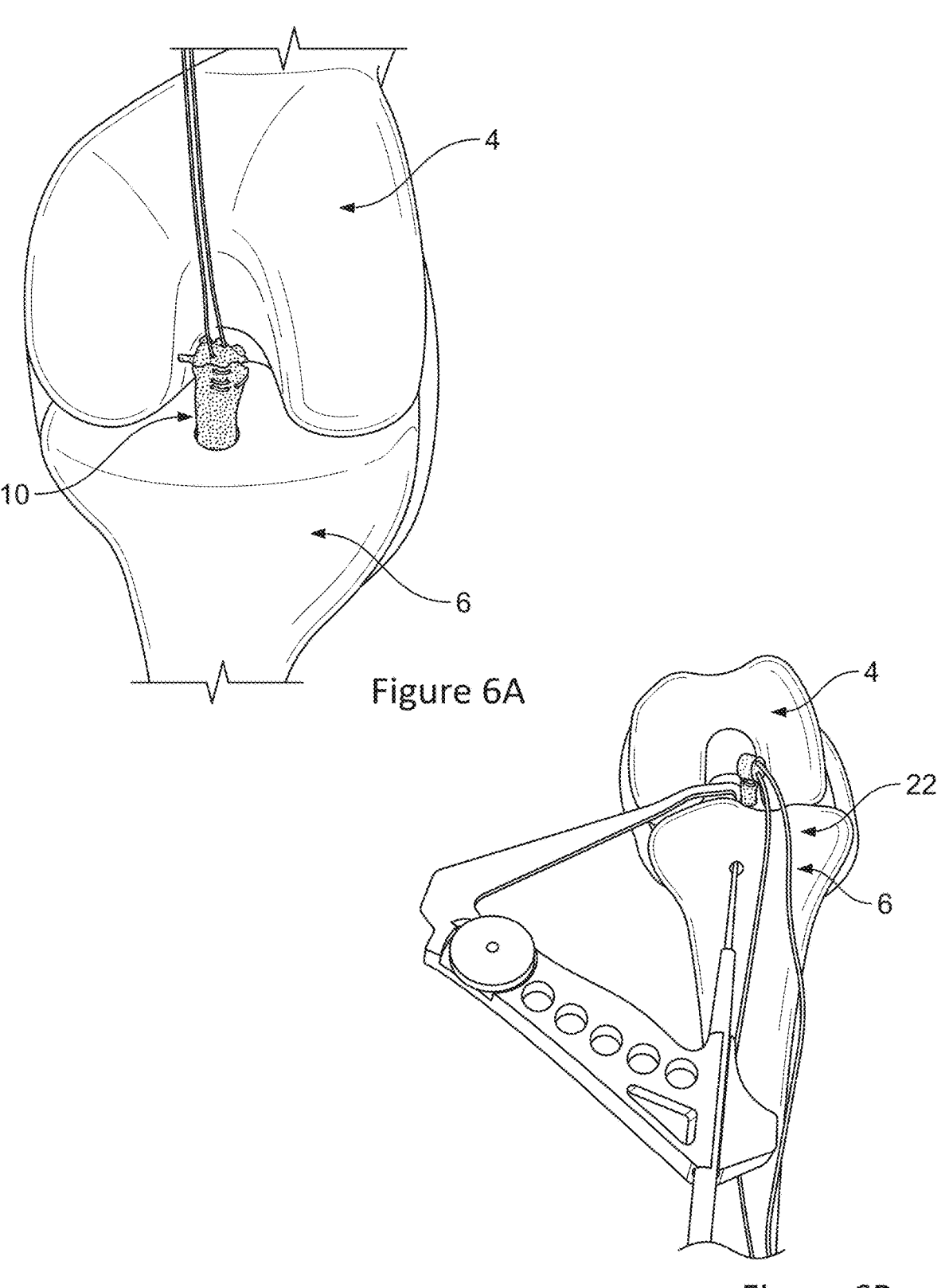
FIG. 6A illustrates suture attachment to the tibial stump in a repair method according to an embodiment of the present disclosure.
FIG. 6B illustrates forming a drill hole in the tibia in a repair method according to an embodiment of the present disclosure.
Figure 6C:
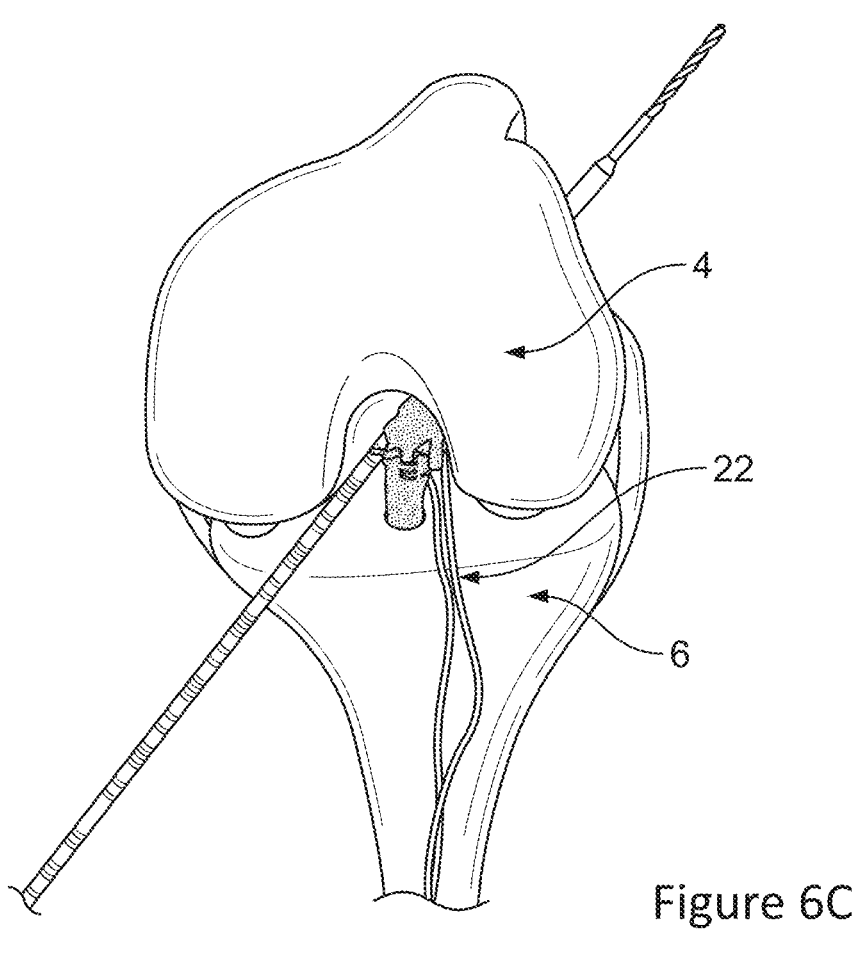
FIG. 6C illustrates forming a drill hole in the femur in a repair method according to an embodiment of the present disclosure.
Figure 6D:
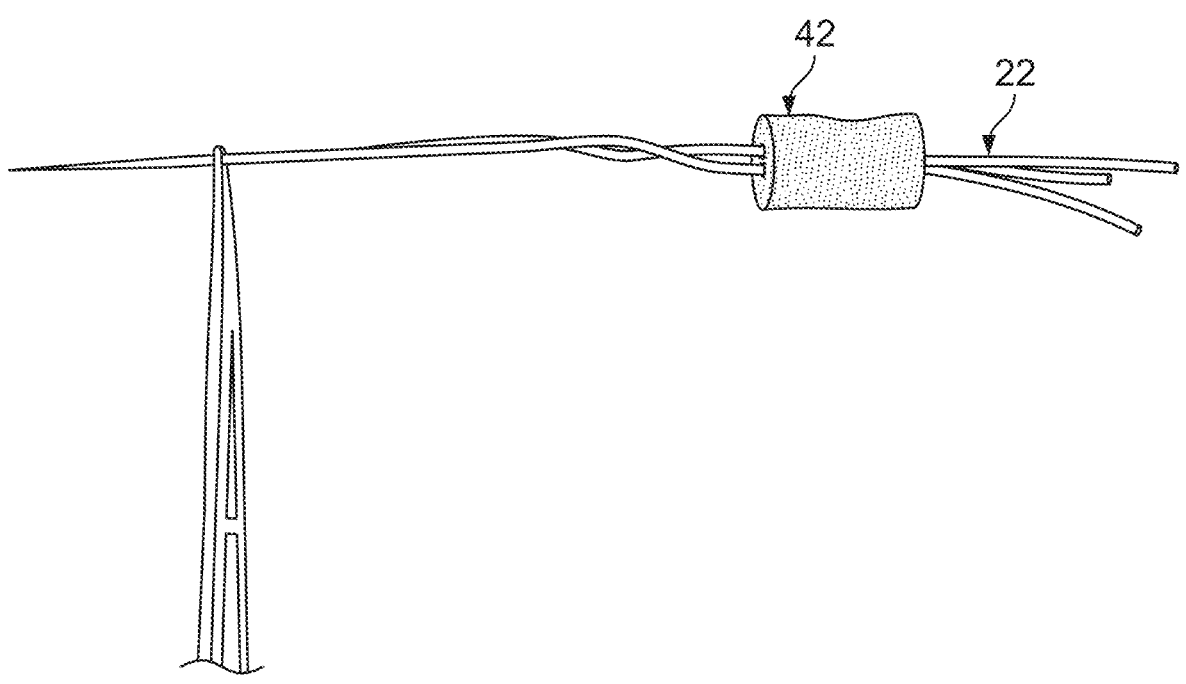
FIG. 6D illustrates threading a scaffold along a suture in a repair method, according to an embodiment of the present disclosure.
Figure 6E:
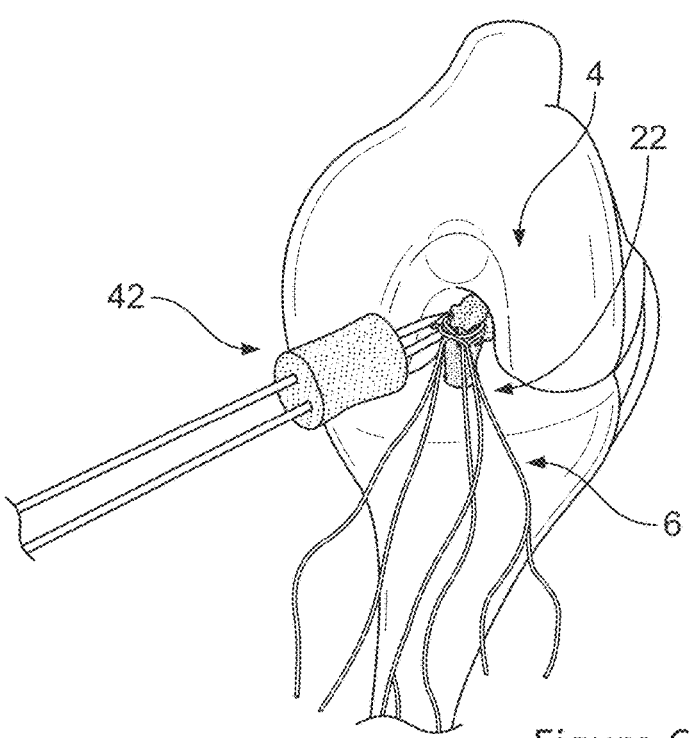
FIG. 6E illustrates positioning the scaffold in the femoral notch in a repair method, according to an embodiment of the present disclosure.
Figure 6F:
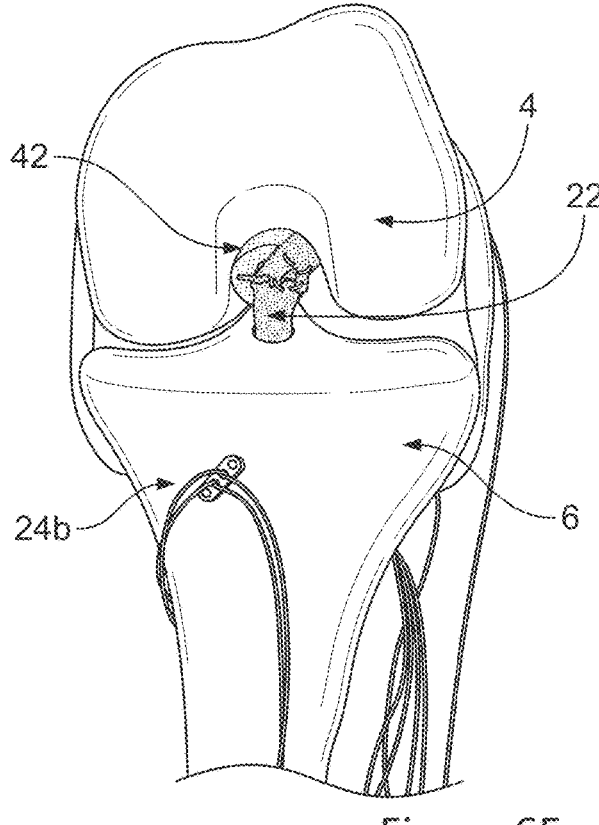
FIG. 6F illustrates positioning the scaffold the scaffold in position and repair material incorporated therein, according to an embodiment of the present disclosure.

As shown in FIGS. 3 and 5, the repair system 40 includes one or more sutures 22. In one example, a set of sutures 22 may be used. For instance, the repair system includes a first suture 22a for coupling to and engagement with the femur and the tibia, a second suture (not shown) for coupling to and engagement with tibial stump and the femur, and additional passing sutures 22 to facilitate insertion of the fixation devices during the procedure. Each suture may have a different color to aid in identifying the sutures during the procedure.

The sutures 22 may be bioabsorbable, such that the subject is capable of breaking down the suture and absorbing it, and synthetic such that the suture may not be from a natural source. The suture 22 may be permanent such that the subject is not capable of breaking down the suture and the suture remains in the subject. A suture 22 may be rigid or stiff or may be stretchy or flexible. A suture 22 may be round in shape or it may have a flat cross section. Examples of sutures include, but are not limited to, VICRYL™ polyglactin 910, PANACRYL™ absorbable suture, ETHI-BOND® EXCEL polyester suture, PDS® polydioxanone suture and PROLENE® polypropylene suture. Sutures are available commercially from manufacturers such as MITEK PRODUCTS division of ETHICON, INC. of Westwood, Mass. Both bioabsorbable and nonabsorbable sutures may be used in aspects of the present disclosure. The selection and use of a type of suture may depend on the application in aspects of the present disclosure.

Continuing with FIGS. 3 and 5, one or more fixation devices 24 may be used in repair system 40. A fixation device 24 may be any device that can be coupled to suture, bone, or both the suture and bone. However, the fixation device needs to not be capable of engagement with cortical and cancellous bone. For instance, as illustrated in FIG. 5, the fixation device 24 can lie adjacent to the bone surface, such as in the form a button. The fixation device 24 can therefore be an anchor, staple, screw, button or other similar device or a knot (tying the suture over a bony bridge). The body of a fixation device 24 may be varied in length. A fixation device may be attached to a bone by physical or mechanical methods as known to those of ordinary skill in the art.

In one example as illustrated in FIG. 5, the repair system 40 includes a first fixation device 24a configured to be placed adjacent to a surface of a femur 4, and a second fixation device 24b configured to be placed adjacent to a surface of the tibia 6, as shown in FIG. 5. Reference number 24 may be used interchangeably with reference number 24a and 24b to refer to a fixation device. As shown, the first and second fixation devices 24a and 24b are similar. In alternative embodiments, the first and second fixation devices 24a and 24b may be different, e.g. a button and screw. In alternative embodiments, the fixation devices may be within the bone of the femur or tibia rather than adjacent to the cortex. In the example described above, the illustrated fixation devices 24a and 24b each include an elongated body having opposed first and second surfaces (not numbered), and at least four holes that extend from the first surface to the second surface. The sutures 22 may be selectively routed through the holes as needed.

The fixation device 24 may be composed of a non-degradable material, such as metal, for example titanium 316 LVM stainless steel, CoCrMo alloy, or Nitinol alloy, or plastic. The fixation device may also alternatively be bioabsorbable such that the subject is capable of breaking down the fixation device and absorbing it. Examples of bioabsorbable material include, but are not limited to, MONOCRYL (poliglecaprone 25), PDS II (polydioxanone), surgical gut suture (SGS), gut, coated VICRYL (polyglactin 910, polyglactin 910 braided), human autograft tendon material, collagen fiber, POLYSORB, poly-L-lactic acid (PLLA), poly-lactic acid (PLA), polysulfone, polylactides (Pla), racemic form of polylactide (D,L-Pla), poly(L-lactide-co-D,L-lactide), 70/30 poly(L-lactide-co-D,L-lactide), polyglycolides (PGa), polyglycolic acid (PGA), polycaprolactone (PCL), polydioxanone (PDS), polyhydroxyacids, and resorbable plate material (see e.g. Orthopedics, October 2002, Vol. 25, No. 10/Supp.). The fixation device may be bioabsorbed over a period of time which includes, but is not limited to, days, weeks, months or years.

Regardless of any particular implementation, a wide range of fixation devices may be used. Examples of a fixation devices, include but are not limited to, IN-FAST™ Bone Screw System (Influence, Inc., San Francisco, Calif.), IN-TAC™ Bone Anchor System (Influence, Inc., San Francisco, Calif), Model 3000 AXYALOOP™ Titanium Bone Anchor (Axya Medical Inc., Beverly, Mass.), OPUS MAGNUM® Anchor with Inserter (Opus Medical, Inc., San Juan Capistrano, Calif), ANCHRON™, HEXALON™ TRINION™ (all available from Inion Inc., Oklahoma City, Okla.) endobuttons and TwinFix AB absorbable suture anchor (Smith & Nephew, Inc., Andover, Mass.). Fixation devices may be available commercially from manufacturers such as Influence, Inc., San Francisco, Calif., Axya Medical Inc., Beverly, Mass., Opus Medical, Inc., San Juan Capistrano, Calif, Inion Inc., Oklahoma City, Okla., Arthrex (Naples Fla.), and Smith & Nephew, Inc., Andover, Mass.

Figure 4A:
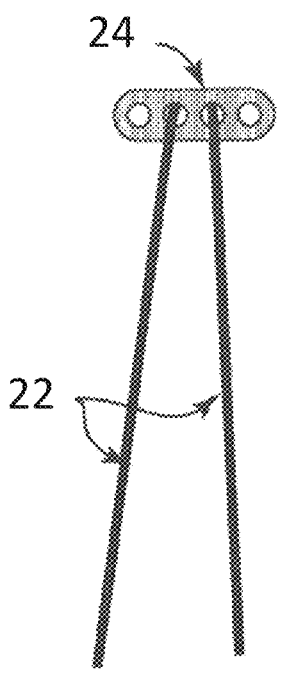
FIG. 4A is a schematic view of a suture attached to fixation device with the fixation device in a plan view, according to an embodiment of the present disclosure.
Figure 4B:
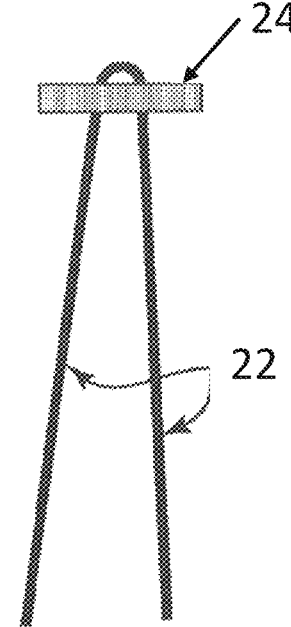
FIG. 4B is another schematic view of the construct shown in FIG. 4A, illustrating a side view of the fixation device.

Embodiments of the present disclosure provide methods of repairing a ruptured ligament 2 involving drilling a hole 20 at or near a repair site 26 of a ruptured ligament 2. A bone at or near a repair site is one that is within close proximity to the repair site and can be utilized using the methods and devices of the present disclosure. For example, a bone at or near a repair site of a torn anterior cruciate ligament is a femur 4 and/or a tibia 6. A hole can be drilled into the femur and/or tibia bone using a device such as a Kirschner wire (for example a small Kirschner wire) and drill, or microfracture pics, or awls. In aspects of the present disclosure the hole may extend into a bone or transverse the bone to form a tunnel. More specifically, during a surgical procedure, a hole 20 may be drilled into a bone on the side facing the repair site or the opposite side to the repair site 26. For instance, a first hole 20a may be formed in the femur. A suture 22a may be passed through the hole 20a in the bone, from either end, and attached to the bone by means of a fixation device 24a on the opposite side of the bone from the repair site. A scaffold 42 may be attached to or slid along the suture 22a to secure the scaffold 42 between the bone 4 and a torn portion or tibial stump 10 of a ruptured ligament 2. A scaffold 42 may be attached to one or both portions of a torn ligament or torn ends of a ruptured ligament 2 by one or more sutures 22. A second hole 20b may be formed in the tibia 6. A second suture 22b may be passed through the hole 20b and held in place with a second fixation device 24b. Thus, the second suture 22b may be attached to a second bone (the tibia 6) at or near the repair site 26. In a preferred embodiment, the same suture 22a may go through both a femoral and tibial tunnel and may be secured in place using a bony fixation device adjacent to each bone (i.e. 24a adjacent to the femur and 24b adjacent to the tibia). In the embodiment shown in FIG. 5, the first and second fixation devices 24a and 24b are buttons, such as an endobutton. Referring back to FIGS. 4A and 4B, it shown in how the suture 22 may be assembled on an exemplary fixation device, here a button. A suture 22 passed through one hole of a button 24 and back through a second hole to anchor the suture, leaving two free suture ends which can exit the bone into the repair site 26. FIG. 4A shows a button en face. FIG. 4B shows a side view of the button. The suture ends may be optionally passed through the repair material prior to being attached to the tibia, or may pass directly to the tibia for fixation and the scaffold or repair material placed adjacent to the suture.

In addition, one or more additional holes may be drilled into a bone surrounding a repair site to promote bleeding into the repair site. The repair can be supplemented by drilling holes into the surrounding bone to cause bleeding. Encouraging bleeding into the repair site may promote the formation of blood clots and enhance the healing process of the injury.

FIGS. 6A-6F is a set of photographs illustrating an exemplary method of the present disclosure using a scaffold and incorporating a stitch in the tibial ACL stump. In aspects of the present disclosure, the tibial stump length is the linear distance from the center of the tibial attachment site to the most superior fibers of the tibial remnant. In certain embodiments of the present disclosure, the methods of the present disclosure involve repair of an ACL with a tibial stump length less than 75% of the total length of the ACL, preferably less than 50%, less than 25%, and less than 10% of the total length of the ACL. In aspects of the present disclosure, the methods of the present disclosure involve repair of an ACL with a tibial stump length greater than 5% of the total length of the ACL. In aspects of the present disclosure, the methods of the present disclosure involve repair of an ACL with a tibial stump length of about 75% to 5% of the total length of the ACL, preferably about 50% to 5%, about 25% to 5%, and about 10% to 5% of the total length of the ACL.

Arthroscopy for meniscal, other pathology may be performed as shown in FIG. 5B. A medial mini-arthrotomy is performed and whip stitch is placed into a tibial stump (ACL remnant on the tibia in a complete tear or rupture). In a partial tear, the whip stich is placed into the torn portion of the ACL. In FIG. 5C a Tibial Tunnel is drilled. A Tibial Pin is placed adjacent to ACL stump using an aiming device and overdrilled with a reamer that has sufficient diameter to allow for suture passage through the tunnel. In FIG. 5D a guide pin is placed just anterior to the femoral insertion site of ACL and the proximal cortex is drilled through, followed by overdrilling with a reamer that has sufficient diameter to allow for button passage through the tunnel. In FIG. 5E, a proximal cortical button is assembled with sutures. Vicryl passing loops are placed through outer holes and non-absorbable Core sutures are placed through inner holes. The sutures that have been attached to the ACL tissue are passed thru central holes. Vicryl Passing Sutures are put in outer holes and sutures via ACL whip stitch through central holes. In FIG. 5F the cortical button is passed through femoral tunnel and engaged on proximal cortex. In FIG. 5G a straight needle is used to thread scaffold onto the Core Sutures. The free ends of Core sutures were passed through tibial tunnel. In FIG. 5H a scaffold is passed up into notch along the Core sutures. The tibial stump is kept anterior to scaffold. Autologous blood (10 cc) is added to the scaffold. In alternative embodiments, autologous blood may be added to the scaffold before the scaffold is passed up into the notch. In FIG. 5I, the knee was extended and the core sutures were pulled down and tied over a second cortical button on the anterior cortical surface of the tibia. The Tibial stump of ACL remains anterior to scaffold. In FIG. 5J the ACL stump sutures were pulled proximally to pull the ACL into the scaffold. The sutures to the tibial stump were tied using an arthroscopic locking knot down onto the proximal femur to secure the ACL in place.

Different from ACL reconstruction, the method of the present disclosure involves repair of the ACL ligament where there are remnants of the ACL still attached to a bone. A hole or tunnel drilled into a bone in the repair method of the present disclosure is not for graft insertion as in ACL reconstruction. Instead, a suture is fixed to or through a hole or tunnel in the method of the present disclosure to hold one or more torn portion of the ACL or a scaffold in place within the intercondylar notch. In conducting further trials and experiments with the method of the present disclosure, the inventors surprisingly found that the optimal point for fixing a suture or for forming a hole or tunnel is not within the ACL footprint at both ends of the ACL insertion sites. In an embodiment of the present disclosure, the point for fixation of a suture or for forming a hole or tunnel on the femur is near the femoral ACL footprint and preferably near the anterior rim of the femoral ACL footprint. In other embodiments of the present disclosure, the point for fixation of a suture or for forming a hole or tunnel on the tibia is between the tibial spines and in the front half of the ACL tibial footprint, preferably between the tibial spines and in the front half or third of the ACL tibial footprint.

Figure 7A:
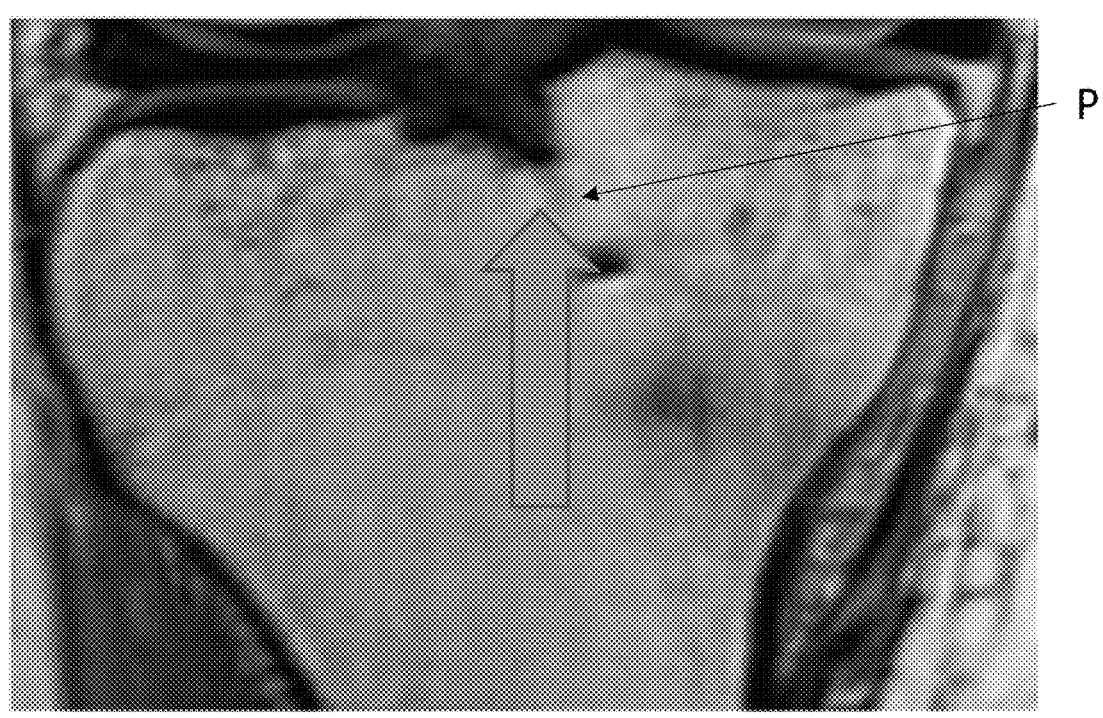
FIG. 7A is a magnetic resonance image showing an anteroproximal view of a point for fixation of suture or for tunnel formation in the tibia between the tibial spines.
Figure 7B:
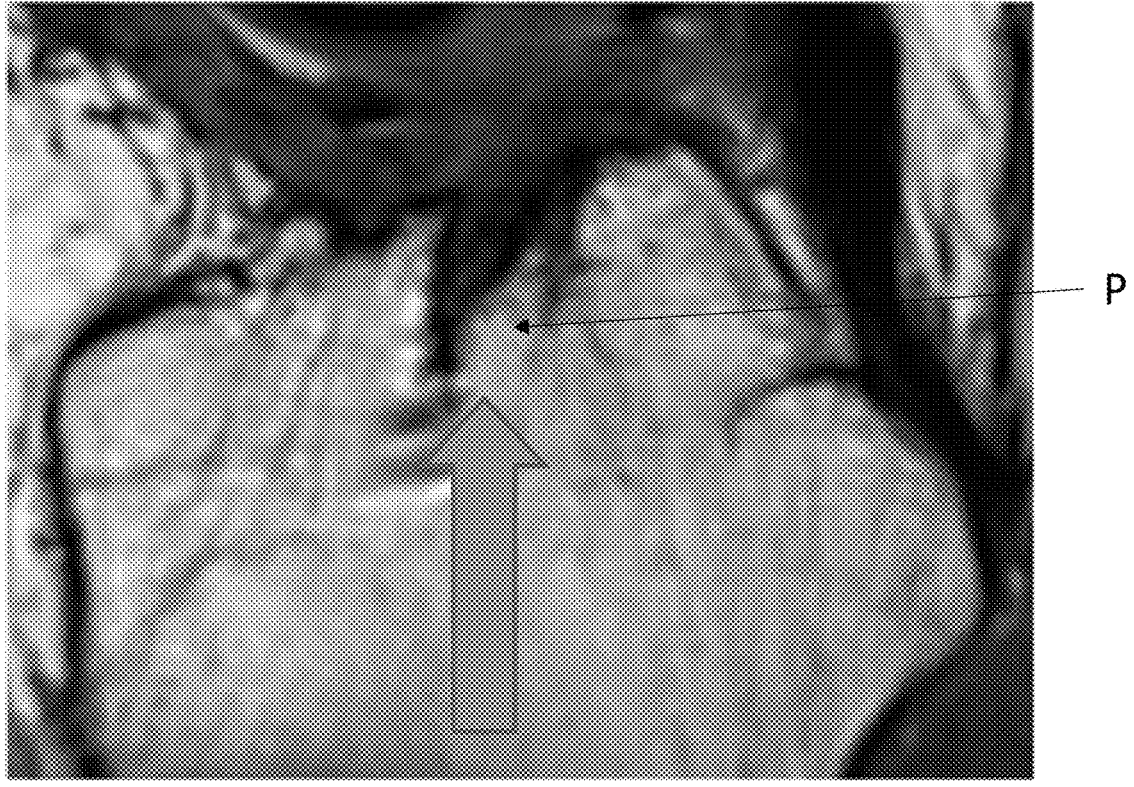
FIG. 7B is a magnetic resonance image showing a lateral view of a point for fixation of suture or for tunnel formation within the tibial ACL footprint.

FIG. 7A is a coronal magnetic resonance imaging (MM) of the tibia showing an anteroproximal view of a point P for fixation of suture or for tunnel formation P in the tibia between the tibial spines. FIG. 7B is a sagittal Mill of the tibia showing a point P for fixation of suture or for tunnel formation within the tibial ACL footprint.

Surprisingly, the inventors found that notchplasty may improve the outcomes of repair using the methods of the present disclosure. Larger notchplasty, the difference between the maximum notch width taken at multiple locations from the middle to the bottom of the notch in the surgical knee and contralateral ACL-intact knee, resulted in a greater cross-sectional area of the repaired ligament on Mill. A higher cross-sectional area of the healing ligament is predictive of a higher maximum load and linear stiffness. Notchplasty during the repair method of the present disclosure may therefore promote more robust healing of the ligament and potentially allow for increased strength of the healed ligament compared to the native intact ACL. In an embodiment of the present disclosure, notchplasty is performed during repair. In other embodiments of the present disclosure, notchplasty is performed around the femoral insertion site of the ACL. In other embodiments of the present disclosure, notchplasty removes bone material from the posterior portion of the intercondylar notch. In other embodiments of the present disclosure, notchplasty removes bone material from the anterior portion of the intercondylar notch. In other embodiments of the present disclosure, notchplasty removes bone material from the inferior portion of the intercondylar notch. In other embodiments of the present disclosure, notchplasty removes bone material from the lateral wall of the intercondylar notch. In other embodiments of the present disclosure, notchplasty removes about 0.5-8 mm of bone from the intercondylar notch, preferably about 1-6 mm, and more preferably about 2-5 mm. In a preferred embodiment of the present disclosure, notchplasty removes at least 3 mm anteriorly and at least 1 mm posteriorly and inferiorly from the lateral wall of the intercondylar notch. In other embodiments of the present disclosure, notchplasty removes bone material from around the femoral insertion site of the ACL to create a kidney bean shaped space. In other embodiments of the present disclosure, notchplasty removes as much bone material as would be performed for a 9 mm diameter hamstring graft in ACL reconstruction.

A scaffold device can be pretreated with a repair material prior to implantation into a subject. The scaffold may be soaked in a repair material prior to or during implantation into a repair site. The repair material may also be injected directly into the scaffold prior to or during implantation. The repair material may be injected within a tubular scaffold at the time of repair. Repair material includes, but is not limited to, a gel, for example a hydrogel, a liquid, or collagen. A liquid includes any material capable of forming an aqueous material, a suspension or a solution. A repair material may include additional materials, such as growth factors, antibiotics, insoluble or soluble collagen (in fibrous, gel, sponge or bead form), a cross-linking agent, thrombin, stem cells, a genetically altered fibroblast, platelets, water, plasma, extracellular proteins and a cell media supplement. The additional repair materials may be added to affect cell proliferation, extracellular matrix production, consistency, inhibition of disease or infection, tonicity, cell nutrients until nutritional pathways are formed, and pH of the repair material. All or a portion of these additional materials may be mixed with the repair material before or during implantation, or alternatively, the additional materials may be implanted proximate to the defect area after the repair material is in place.

In certain embodiments, a repair material may include collagen and one or more blood cells, i.e. white blood cells (WBC), platelets, or whole blood). In some embodiments, WBC, platelets, or whole blood are derived from the subject to be treated. In other embodiments, WBC, platelets, or whole blood are derived from a donor that is allogeneic to the subject. In certain embodiments, WBC, platelets, or whole blood may be obtained as platelet rich plasma (PRP). In a non-limiting example, WBC, platelets, or whole blood may be isolated from a subject's blood using techniques known to those of ordinary skill in the art. As an example, a blood sample may be centrifuged at 700 rpm for 20 minutes and the platelet-rich plasma upper layer removed. Platelet density may be determined using a cell count as known to those of ordinary skill in the art. WBCs or whole blood may be obtained using similar techniques known to the skilled artisan. The platelet rich plasma may be mixed with collagen and used as a scaffold. The platelet rich plasma may be mixed with any one or more of the scaffold materials of the present disclosure.

In other embodiments, the repair material is autologous blood. In other embodiments, the repair material is composed of white blood cells, red blood cells, platelets or plasma. In other embodiments, the repair material is composed of monocytes, eosinophils, basophils or neutrophils.

In other embodiments, the repair material is a modified blood composition. In other embodiments, the repair material is composed of autologous blood which has been treated after removal from the patient to increase or decrease the presence of a specific type of white blood cell within the repair material. In one embodiment, the blood has been treated to increase the presence of monocytes in the repair material. In one embodiment, the blood has been treated to decrease the presence of eosinophils in the repair material. In other embodiments, the patient has been treated prior to surgery to increase the presence of white blood cells and/or platelets in the circulating blood that is drawn to use for the repair material. In other embodiments, the type of modified blood composition to introduce to a scaffold is dependent on a patient's sex. In other embodiments in the method of the present disclosure, a modified eosinophil blood composition is utilized in a male patient. In other embodiments in the method of the present disclosure, a modified monocyte blood composition is utilized in a female patient.

The devices of the present disclosure may be used in surgical procedures. The following is an example of a surgical procedure which may be performed using the devices and methods of the present disclosure. The affected extremity is prepared and draped in the standard sterile fashion. A tourniquet may be used if indicated. Standard arthroscopy equipment may be used. After diagnostic arthroscopy is performed, and the intra-articular lesion identified and defined, the tissue ends are pretreated, either mechanically or chemically, and the scaffold introduced into the tissue defect. The scaffold is then bonded to the surrounding tissue using the methods described herein. This can be done by the addition of a chemical agent or a physical agent such ultraviolet light, a laser, or heat. The scaffold may be reinforced by placement of sutures or clips. The arthroscopic portals can be closed, and a sterile dressing placed. The post-operative rehabilitation is dependent on the joint affected, the type and size of lesion treated, and the tissue involved.

In some embodiments, two separate techniques are combined to affect the repair. A first construct is used to bring the femur and tibia into correct alignment, in either the coronal or sagittal plane or both, and a second construct is used to bring one or both of the torn ACL ends closer to the other end. In the preferred embodiment, one or more sutures are secured to both femur and tibia and used to bring the joint into anatomic alignment in the sagittal plane, and a second suture placed through the tibial ACL stump and used to bring the tibial ACL stump closer to the femoral stump. Prior to bringing the tibial stump closer to the femoral stump, in the preferred embodiment, blood is added to a biodegradable scaffold, which is then placed in the notch—preferably using the first set of sutures to help secure it in place, and the suture in the tibial stump is used to pull the tibial stump up into the scaffold as it rests in the notch.

The device of the present disclosure may be used with arthroscopic equipment. The device of the present disclosure may be used by insertion through an open incision. The scaffold is compressible to allow introduction through arthroscopic portals, incisions and equipment. The scaffold can also be pre-treated in antibiotic solution prior to implantation.

Post-operation or repair of the ACL ligament, a subject undergoes physical therapy to regain strength and function. An example of a physical therapy protocol is one adapted from the Multicenter Orthopedic Outcomes Network (MOON) for ACL reconstruction. Generally, physical therapy is not initiated until 2 weeks post reconstruction (replacement of the torn ACL with a graft of tendon). One early focus of physical therapy after an ACL reconstruction is regaining quadriceps function and strength. Surprisingly, the inventors found that delaying physical therapy may improve outcomes in the repair method of the present disclosure. In an embodiment of the present disclosure, physical therapy is delayed post repair. In other embodiments, the delay in physical therapy focuses on limiting the early recovery of quadriceps strength. In other embodiments, physical therapy is delayed to 3 to 12 weeks post repair, preferably 4 to 12 weeks, 6-12 weeks, 8-12 weeks, 10-12 weeks, and 12 weeks post repair.

A subject includes, but is not limited to, any mammal, such as human, non-human primate, mouse, rat, dog, cat, horse or cow. In certain embodiments, a subject is a human.

EXAMPLES

Example 1: MRI Assessment of Patients' Knees 6 Months after ACL Repair

Mill has been used in the past for evaluating the quality of the graft in ACL reconstruction and associated outcomes. Mill is also demonstrated to be useful for predicting the size and mechanical properties of the healing ACL in ACL repair. The average cross-sectional area of the ACL ligament can be measured using MM and is an indicator of the amount of tissue and size of the ligament, either in its intact state or when healing after an injury and repair. A higher cross-sectional area of the healing ligament is predictive of a higher maximum load and linear stiffness. The signal intensity, normalized to cortical bone, is an indicator of the quality of the tissue. The lower signal intensity on a gradient echo sequence is predictive of a higher ACL maximum load and linear stiffness values.

Methods 65 patients aged 14 to 35 years who had a complete ACL tear, who were fewer than 45 days from injury, who had closed physes, and who had at least 50% of the length of the ACL attached to the tibia (as determined from a preoperative Mill) underwent a scaffold-augmented ACL repair procedure (bridge-enhanced ACL repair [BEAR]). Patients were excluded from enrollment if they had a history of knee surgery, a history of infection in the knee, or risk factors that might adversely affect ligament healing (nicotine/tobacco use, corticosteroids in the past 6 months, chemotherapy, diabetes, inflammatory arthritis). Patients were excluded if they had a displaced bucket-handle tear of the medial meniscus requiring repair; however, all other meniscal injuries were included. Patients were also excluded if they had a full-thickness chondral injury, a grade 3 medial collateral ligament injury, a concurrent complete patellar dislocation, or an operative posterolateral corner injury. A total of 3 patients were excluded for the current report due to artifact or blurry images on the MRI or loss to follow-up, leaving 62 patients for analysis. Patient recruitment was completed over an 11-month period.

Surgical Procedure

After the induction of general anesthesia, an examination was performed to verify the positive pivot shift on the injured side and to record the Lachman test, range of motion, and pivot-shift examination results on both knees. A tourniquet was then applied to the surgical limb. A knee arthroscopy was performed, and any meniscal injuries present were treated. A tibial aimer (Acufex Director Drill Guide; Smith & Nephew) was used to place a 2.4-mm guide pin through the tibia and the tibial footprint of the ACL. The pin was overdrilled with a 4.5-mm reamer (Endoscopic Drill; Smith & Nephew). A notchplasty was performed through use of a combination of shaver and curette to facilitate visualization of the femoral footprint. A guide pin was then placed in the femoral ACL footprint, drilled through the femur, and then overdrilled with the 4.5-mm reamer. A 4-cm arthrotomy was made at the medial border of the patellar tendon, and a whipstitch of No. 2 absorbable braided suture (Vicryl; Ethicon) was placed into the tibial stump of the torn ACL. Two No. 2 nonabsorbable braided sutures (Ethibond; Ethicon) were looped through the 2 center holes of a cortical button (Endobutton; Smith & Nephew). The free ends of a No. 2 absorbable braided suture from the tibial stump were passed through the cortical button, which was then passed through the femoral tunnel and engaged on the lateral femoral cortex. Both looped sutures of No. 2 nonabsorbable braided material (4 matched ends) were passed through the scaffold, and 10 mL of autologous blood obtained from the antecubital vein was added to the scaffold. The scaffold was then passed up along the sutures into the femoral notch, and the nonabsorbable braided sutures were passed through the tibial tunnel and tied over a second cortical button on the anterior tibial cortex with the knee in full extension. The remaining pair of suture ends coming through the femur were tied over the femoral cortical button to bring the ACL stump into the scaffold by use of an arthroscopic surgeon's knot and knot pusher. The arthrotomy was closed in layers and the tourniquet deflated. Sterile dressings, followed by a cold therapy unit (Polar Care; Breg) and locking hinge knee brace (T-scope; Breg), were applied. No surgical drain was used.

Magnetic Resonance Imaging

MRI scans were acquired preoperatively and from all operated knees at 6 months after surgery. A 3.0-T scanner (Tim Trio; Siemens) and a 15-channel knee coil (Siemens) were used to obtain the following sequences: sagittal and coronal proton density fast spin echo (repetition time [TR]/ echo time [TE], 3000/9.7 ms; field of view [FOV], 16 cm; 3 skip 0.3 slice/gap; matrix, 284×384 [phase×frequency]; and echo train length, 4) and a 3-dimensional (3D) constructive interference in steady state (CISS) (TR/TE, 14/7 ms; flip angle, 35°; FOV, 16 cm, 100×384×284 [slice×frequency× phase]). Images of the surgical and contralateral knees from the CISS sequence were used to measure notchplasty in 56 of the 62 patients. One patient had no contralateral image obtained and 5 patients had contralateral images obtained but not used because the contralateral knee had undergone ACL reconstruction (n=4) or the image was too noisy (n=1). It was assumed that the contralateral notch width represented the preoperative notch width of the surgical knee.

Candidate Independent Variables (Predictor Variables)

Preoperatively, the patients' sex, age, BMI, and mechanism of injury were recorded. All patients completed questionnaires to determine the International Knee Documentation Committee (IKDC) Subjective Score (https:// www.sportsmed.org/AOSSMIMIS/members/downloads/ research/IKDCEnglishUS.pdf) and Marx Activity Score (https://www.aaos.org/uploadedFiles/PreProduction/Quality/Measures/pdf-MARX%20SCALE-%20english.pdf). The preoperative Mills were used to measure the femoral stump length, tibial stump length, and posterior tibial slope. At 3 months postoperatively, the quadriceps and hamstring strengths for both the surgical and the contralateral control legs were measured by a physical therapist using a handheld dynamometer (Microfet 2; Hoggan Scientific LLC). The quadriceps strength was measured with the patient seated and the knee supported at 90° of flexion. The dynamometer was placed at the distal tibia, and the patient was instructed to extend the knee with maximum effort. The hamstring strength was measured with the patient prone and the knee in 90° of flexion. The dynamometer was placed at the ankle, and the patient was instructed to pull the foot toward the hip with maximum effort. Muscle strength values were presented as the percentage of the contralateral uninjured control leg.

MRI Measurements (Dependent Variables)

The measurements of cross-sectional area and signal intensity were obtained from the 3D CISS sequence obtained at 6 months after BEAR. The average cross-sectional area of the ligament was calculated by manually segmenting the ACL in 3D and dividing the volume by the ACL length measured from the 3D model. The median ACL signal intensity was calculated from the segmented ACL mask and then normalized to the patient-specific signal intensity of the posterior cortex of the femoral shaft to minimize interscan variability. The intraclass correlation coefficients between 2 independent observers for the normalized signal intensity and average cross-sectional area measurements were 0.909 and 0.959, respectively.

Results

A larger cross-sectional area of the repaired ligament at 6 months was associated with male sex, older age, and the performance of a larger notchplasty (p<0.05 for all associations). A lower signal intensity at 6 months, indicating greater similarity to normal ligament and a higher tensile strength of the ligament material, was associated with a smaller tibial slope and greater side-to-side difference in quadriceps strength 3 months after surgery. Other factors, including preoperative body mass index, mechanism of injury, tibial stump length, and Marx activity score, were not significantly associated with either MRI parameter at 6 months.

Example 2: Cohort Study of White Blood Cells and Platelet Concentrations on Healing Ligament Cross-Section Area and Signal Intensity 6 Months after BEAR ACL Repair Methods Sixty-one patients underwent MRI imaging six months after surgery. The normalized signal intensity and average cross-sectional area of the healing ligament were measured from an MRI stack obtained using a gradient echo sequence. The results were stratified by sex, and univariate and multivariate regression analyses determined significant correlations between blood cell concentrations on these two MR parameters.

Surgical Procedure

See Example 1 above. In addition, after autologous blood was added to the scaffold an additional 22 ml of blood was drawn and sent to the laboratory for a complete blood count, including a differential count of the specific types of white blood cells.

MR Assessment of ACL Healing

MR images were acquired from all operated knees six months after surgery. Using a 3T scanner (Tim Trio; Siemens, Erlangen Germany) and a 15-channel knee coil, the following sequence was obtained: 3D Constructive Interference in Steady State (CISS; TR/TE=14/7, FA=35, 16 cm FOV, 100×384×384 (slice×frequency×phase)). The postoperative MR images were then used to measure the cross-sectional area and signal intensity of the healing ligament. Briefly, repaired ACLs were manually segmented from the sagittal CISS image stack to create a 3D model of the structure using commercially available software (Mimics 17.0; Maternalize). The model was used to measure the ligament volume and length, which were then used to calculate the average ACL cross-sectional area (Volume/

Length). Median gray scale value of the repaired ACL was then calculated from the segmented ACL mask and normalized to the patient-specific gray scale value of the posterior cortex of the femoral shaft to minimize interscan variability. The normalized value was then reported as ACL signal intensity.

Results

In unadjusted analyses, age and sex were found to correlate with healing ligament cross-sectional area (p<0.04). Adjusted multivariable analyses indicated that in males, a lower eosinophil count correlated with a lower (improved) normalized signal intensity ($\beta$=0.12, p=0.001). In females, a higher monocyte concentration correlated with a higher ACL cross-sectional area ($\beta$=1.01, p=0.049). All other factors measured, including the concentration of platelets, neutrophils, lymphocytes, basophils, and immunoglobulin against Bovine Gelatin were not significantly associated with either MR parameter in either sex (p>0.05).

CONCLUSION

While age, gender and specific white blood cell population concentrations in males and females significantly affected the cross-sectional area of the healing ACL, platelet concentration and prior exposure to bovine collagen did not have any significant effect on cross-sectional area or signal intensity in either sex.

The phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

What is claimed:

1. A method for repairing a tear of an anterior cruciate ligament (ACL), comprising:
   contacting a torn femoral stump of the ACL and a torn tibial stump of the ACL with a compressible and expandable scaffold comprised of a self-assembly of enzyme-solubilized collagen fibers comprising tropocollagen or atelocollagen, the scaffold having a collagen concentration of at least 10 mg/mL,
   wherein the torn tibial stump has a tibial stump length that is less than 75% but greater than 5% of a total length of the ACL, and
   wherein the scaffold is hydrophilic and free of cross links, and
   wherein the content of nucleic acids in the collagen material is less than 20% of that found in a native tissue.

2. The method of claim 1, wherein the tear is a complete tear.

3. The method of claim 1, further comprising delaying physical therapy post repair.

4. The method of claim 3, wherein physical therapy is not initiated until 3 to 12 weeks post repair.

5. The method of claim 3, wherein delaying physical therapy comprises limiting recovery of quadriceps strength.

6. The method of claim 1, wherein the tibial stump length is less than 50% but greater than 5% of the total length of the ACL.

7. The method of claim 1, wherein the torn tibial stump comprises a tibial stump length that is less than 50% of the total length of the ACL.

8. The method of claim 1, wherein the torn tibial stump comprises a tibial stump length that is less than 25% of the total length of the ACL.

9. The method of claim 1, wherein the torn tibial stump comprises a tibial stump length that is less than 10% of the total length of the ACL.

10. The method of claim 1, further comprising performing a notchplasty to a femur.

11. The method of claim 10, wherein notchplasty is performed prior to contacting the torn femoral and tibial stumps of the ACL with the scaffold.

12. The method of claim 1, further comprising performing a notchplasty comprises taking at least 3 mm anteriorly and 1 mm posteriorly and inferiorly from a lateral wall of an intercondylar notch around a femoral insertion site of the ACL.

13. The method of claim 1, further comprising introducing blood to the scaffold.

14. The method of claim 1, further comprising introducing a modified blood composition depending on a patient's sex to the scaffold.

15. The method of claim 14, wherein the modified blood composition is an eosinophil depleted blood composition for a male patient.

16. The method of claim 14, wherein the modified blood composition is a monocyte enriched blood composition for a female patient.

17. The method of claim 1, wherein contacting the torn tibial stump and the torn femoral stump of the ACL with a scaffold comprises:
   securing the torn tibial stump of the ACL to a first suture;
   fixing the first suture and a second suture to a femur near a femoral footprint;
   passing the second suture along the scaffold;
   fixing the second suture to a tibia proximate one or more tibial spines and in a tibial ACL footprint;
   sliding the scaffold along the second suture towards an intercondylar notch to contact the torn femoral stump of the ACL; and
   pulling the torn tibial stump of the ACL to contact the scaffold.

18. The method of claim 17, further comprising introducing a blood composition to the scaffold prior to sliding the scaffold along the second suture.

19. The method of claim 18, further comprising enlarging an intercondylar notch of the femur prior to securing the torn tibial stump of the ACL to the first suture.

20. The method of claim 17, where the scaffold comprises Type I Collagen.

21. The method of claim 17, where the scaffold comprises glycosaminoglycan (GAG).

22. The method of claim 1, wherein contacting the torn portions of the ACL with the scaffold further comprises:
   forming a tibial tunnel at a point on the tibia between the tibial spines and in a tibial ACL footprint;
   forming a femoral tunnel at a point on a femur near a femoral ACL footprint;
   securing the torn tibial stump of the ACL to a first end of a first suture;
   passing a second end of the first suture and a first end of a second suture through the femoral tunnel;
   fixing the second end of the first suture and the first end of the second suture to the femur;
   passing a second end of the second suture through the scaffold and then through the tibial tunnel;
   sliding the scaffold along the second suture towards a back of an intercondylar notch to contact the torn femoral stump of the ACL; and
   fixing the second end of the second suture to the tibia;

pulling the torn tibial stump of the ACL to contact the scaffold.

23. The method of claim 22, wherein the point on the femur is near an anterior rim of the femoral ACL footprint.

24. The method of claim 23, wherein the point in a tibial ACL footprint is halfway back into the tibial ACL footprint.

25. The method of claim 23, wherein the point in a tibial ACL footprint is a third of the way back into the tibial ACL footprint.

26. The method of claim 23, further comprising the step of:

enlarging the intercondylar notch of the femur prior to forming the tibial tunnel.

27. The method of claim 23, further comprising the step of:

introducing a blood composition to the scaffold prior to sliding the scaffold along the second suture.

28. The method of claim 1, where the scaffold comprises Type I Collagen, and is configured to absorb blood.

29. The method of claim 1, where the scaffold comprises glycosaminoglycan (GAG).

30. A method for repairing a tear of an anterior cruciate ligament (ACL), comprising:

performing a notchplasty to a femur such that a larger ACL is formed after repair; and contacting a torn femoral stump of the ACL and a torn tibial stump of the ACL with a compressible and expandable scaffold comprised of a self-assembly of enzyme-solubilized collagen fibers comprising tropocollagen and atelocollagen, the scaffold having a collagen concentration of at least 10 mg/mL; and adding a repair material to the scaffold, wherein the scaffold is hydrophilic and free of cross links, and wherein the content of nucleic acids in the collagen fibers is less than 20% of that found in a native tissue.

31. The method of claim 30, wherein the tear is a partial tear.

32. The method of claim 30, wherein the tear is a complete tear.

33. The method of claim 30, wherein the torn tibial stump comprises a tibial stump length that is less than 75% but greater than 5% of a total length of the ACL.

34. The method of claim 33, wherein the tibial stump length is less than 50% but greater than 5% of the total length of the ACL.

35. The method of claim 30, wherein the notchplasty is performed prior to contacting the torn femoral and tibial stumps of the ACL with the scaffold.

36. The method of claim 35, wherein performing the notchplasty comprises taking at least 3 mm anteriorly and 1 mm posteriorly and inferiorly from the lateral wall of an intercondylar notch around the femoral insertion site of the ACL.

37. The method of claim 30, wherein the repair material is blood.

38. The method of claim 30, wherein contacting the torn portions of the ACL with a scaffold comprises:

securing the torn tibial stump of the ACL to a first suture;

fixing the first suture and a second suture to a femur near a femoral footprint;

passing the second suture along the scaffold;

sliding the scaffold along the second suture towards an intercondylar notch to contact the torn femoral stump of the ACL;

fixing the second suture to a tibia proximate one or more tibial spines and in a tibial ACL footprint; and pulling the torn tibial stump of the ACL to contact the scaffold.

39. The method of claim 30, where the scaffold comprises Type I Collagen.

40. The method of claim 30, where the scaffold comprises glycosaminoglycan (GAG).

*     *     *     *     *